United States Patent
Fukami et al.

(10) Patent No.: US 6,500,835 B2
(45) Date of Patent: Dec. 31, 2002

(54) PREVENTIVE OR THERAPEUTIC DRUGS FOR FIBROSIS CONTAINING CHYMASE INHIBITORS AS THE ACTIVE INGREDIENT

(75) Inventors: Harukazu Fukami, Kyoto (JP); Hideki Okunishi, Izumo (JP); Eiichi Kakizoe, Izumo (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/959,232

(22) PCT Filed: Feb. 22, 2001

(86) PCT No.: PCT/JP01/01321

§ 371 (c)(1),
(2), (4) Date: Oct. 22, 2001

(87) PCT Pub. No.: WO01/62292

PCT Pub. Date: Aug. 30, 2001

(65) Prior Publication Data

US 2002/0183338 A1 Dec. 5, 2002

(30) Foreign Application Priority Data

Feb. 22, 2000 (JP) ........................... 2000-050502

(51) Int. Cl.$^7$ ............................................. A61K 31/517

(52) U.S. Cl. .................................................. 514/266.1

(58) Field of Search ............................. 514/266.1, 262, 514/259, 266.2, 266.21

(56) References Cited

U.S. PATENT DOCUMENTS 5,691,335 A 11/1997 Fukami et al.
5,814,631 A 9/1998 Fukami et al.

FOREIGN PATENT DOCUMENTS

| EP | 795548 A1 | 9/1997 |
|---|---|---|
| WO | 93/03625 A1 | 3/1993 |
| WO | 93/25574 A1 | 12/1993 |
| WO | 96/04248 A1 | 2/1996 |
| WO | 96/33974 A1 | 10/1996 |
| WO | 96/39373 A1 | 12/1996 |
| WO | 97/11941 A1 | 4/1997 |
| WO | 98/18794 A1 | 5/1998 |
| WO | 99/41277 A1 | 8/1999 |
| WO | 00/10982 A1 | 3/2000 |
| WO | 01/32214 A1 | 5/2001 |
| WO | 01/62293 A1 | 8/2001 |
| WO | 01/62294 A1 | 8/2001 |

OTHER PUBLICATIONS

Hideki Okunishi, "Angiotensin II formation by chymase in the cardiovascular tissue," Folia Pharmacologica Japonica, vol. 112, No. 3 (1998), pp. 203–212.

Eiji Ikada, "Roles of ACE and chymase in kidney," Kekkan to Naihi, vol. 9, No. 2 (1999) pp. 177–184.

Eiichi Kakizoe, "Activation of skin chymase in scleroderma model mice," Journal of Pharmacology, vol. 79, No. Suppl.1 (1999) p. 60P.

S. Akimoto, et al, "Dermal mast cells in scleroderma: their skin density, tryptase/chymase phenotypes and degranulation," British Journal of Dermatology, vol. 138, 1998, pp. 399–406.

Anne–Marie A. Irani, et al, "Mast Cell Changes in Scleroderma," Arthritis and Rheumatism, vol. 35, No. 8, Aug. 1992, pp. 933–939.

Melinda Walker, et al, "Mast Cells and Their Degranulation in the Tsk Mouse Model of Scleroderma (42183)," Proceedings of the Society for Experimental Biology and Medicine, vol. 180, 1985, pp. 323–328.

Eric T. Everett, et al, "The Role of mast cells in the development of skin fibrosis in tight–skin mutant mice," Comp. Biochem. Physiol., vol. 110A, No. 2, 1995, pp. 159–165.

Melinda Walker, et al, "Inhibition of Fibrosis in TSK Mice by Blocking Mast Cell Degranulation," The Journal of Rheumatalogy, 14:2, 1987, pp. 299–301.

Amy R. O'Brien–Ladner, et al, "Bleomycin injury of the lung in a mast–cell–deficient model," Agents Actions, vol. 39, 1993, pp. 20–24.

Toshihiko Okazaki, et al, "Increase of Mast Cells in the Liver and Lung May Be Associated with but Not a Cause of Fibrosis: Demonstration Using Mast Cell–Deficient Ws/Ws Rats," Laboratory Investigation, vol. 78, No. 11, Nov. 1998, pp. 1431–1438.

Juhani Saarinen, et al, "Activation of Human Interstitial Procollagenase through Direct Cleavage of the Leu$^{83}$–Thr$^{84}$ Bond by Mast Cell Chymase," The Journal of Biological Chemistry, vol. 269, No. 27, 1994, pp. 18134–18140.

(List continued on next page.)

*Primary Examiner*—Raymond Henley, III
(74) *Attorney, Agent, or Firm*—Burns, Doane, Swecker & Mathis, LLP

(57) ABSTRACT

A medicament for the prevention or treatment containing a chymase inhibitor, as an effective component, which is a side effect-free, safe medicament for prevention or treatment of fibrosis of the skin or various viscera which suppresses the progression of the condition, prevents the progression of complications, and improves the quality of life of the patient, wherein a quinazoline derivative having the formula (I):

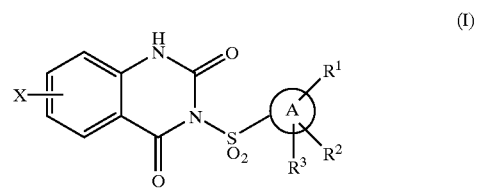

or a pharmaceutically acceptable salt thereof is included therein.

63 Claims, 8 Drawing Sheets

OTHER PUBLICATIONS

Jussi Taipale, et al, "Human Mast Cell Chymase and Leukocyte Elastase Release Latent Transforming Growth Factor-β1 from the Extracellular Matrix of Cultured Huamn Epithelial and Endothelial Cells," The Journal of Biological Chemistry, vol. 270, No. 9, 1995, pp. 4689–4696.

Kevin P. Rioux, et al, "Hepatic Mucosal Mast Cell Hyperplasia in Rats With Secondary Biliary Cirrhosis," Hepatology, vol. 23, No. 4, 1996, pp. 888–895.

Naotaka Shiota, MD PhD, et al, "Tranilast Suppresses Vascular Chymase Expression and Neointima Formation in Baloon–Injured Dog Carotid Artery," Circulation, 99(8), Mar. 2, 1999, pp. 1084–1090.

Masatake Hara, MD, et al, "Mast Cells Cause Apoptosis of Cardiomyocytes and proliferation of Other Intramyocardial Cells In Vitro," Circulation, 100(13), Sep. 28, 1999, pp. 1443–1449.

Naotaka Shiota, et al, "Chymase is activated in the hamster heart following ventricular fibrosis during the chronic stage of hypertension," FEBS Letters, 406, 1997, pp. 301–304.

Thomas Armbrust, et al, "Mast cells distribution in human liver disease and experimental rat liver fibrosis. Indications for mast cell participation in development of liver fibrosis," Journal of Hepatology, vol. 26, 1997, pp. 1042–1054.

PREVENTIVE OR THERAPEUTIC DRUGS FOR FIBROSIS CONTAINING CHYMASE INHIBITORS AS THE ACTIVE INGREDIENT

This is a 371 of PCT/JP01/01321 filed Feb. 22, 2001.

TECHNICAL FIELD

The present invention relates to a medicament for the prevention or treatment of fibrosis involving extracellular matrix dysbolism, a pharmaceutical composition for the prevention or treatment of fibrosis involving extracellular matrix dysbolism, and a medicament for alleviation of extracellular matrix dysbolism.

BACKGROUND ART

Fibrosis is a disease characterized by excessive deposition of connective tissue-protein involving extracellular matrix dysbolism in the skin and other organs such as the lungs, heart, liver, and kidneys. For example, hepatic fibrosis is a disease characterized by the excessive deposition of collagen and other connective tissue proteins in the liver. Diseases leading to hepatic fibrosis include vairal hepatitis, alcoholic liver disease, schistosomiasis etc. In these diseases, the connective tissue protein gradually accumulates in the hepatic tissue. As a result, disorders in the hepatic functions occur and finally lead to cirrhosis (*J. Hepatol.* 8, 115, 1989). On the other hand, scleroderma and other skin fibrosis are conditions characterized by the excessive deposition of collagen and other connective tissue protein in the epidermis of the skin. The cause of skin fibrosis includes various skin diseases such as chronic inflammation and chronic autoimmune reactions, and various skin injury such as mechanical wounds and burns (*J. Rheumatol.* 15, 202, 1988). Further, pulmonary fibrosis is a condition characterized by the excessive deposition of collagen or other connective tissue proteins in the lungs and is induced by pneumonia medicamentosa caused by chemotherapeutic agents such as anti-tumor drugs and antibiotics (*Am. J. Pathol.* 259, L159, 1990).

The mechanism of pathogenesis of fibrosis have not yet been sufficiently elucidated at the present. In general, the proliferation and function of fibroblasts are closely controlled in normal conditions. However, in pathological state in which inflammation or tissue injury is serious or sustained, the tissue repair mechanism goes into overdrive and the control mechanism is abrogated (*Int. J. Biochem. Cell Biol.* 29, 79, 1997). Excessive tissue repair is caused by over-production of connective tissue protein probably due to abnormal proliferation of fibroblasts and extracellular matrix dysbolism. The cytokines causing such a phenomenon include, fibroblast growth factor (FGF family), transforming growth factor (TGF-β), platelet derived growth factor (PDGF), etc. (*FASEB J.* 8, 854, 1994). In recent years, numerous studies have been performed to obtain the substances inhibiting the production or the activity of such cytokines, but no inhibitors have yet been applied to human. Further, anti-inflammatory agents such as steroid have been used to treat fibrosis with the aim of suppressing chronic inflammation, but they cannot be said to be sufficiently satisfactory in terms of efficacy and side effects. A superior medicament for the treatment of fibrogenesis is therefore needed.

On the other hand, chymase is a serine protease stored in mast cell granules, and widely present in tissue such as the skin, heart, vascular walls, intestines, etc. (*Mast Cell Proteases in Immunology and Biology;* Caughey, G. H., Ed; Marcel Dekker, Inc.; New York, 1995). Numerous findings that suggest chymase is involved in various types of fibrosis have already been reported. For example, it has been reported that administration of cromoglycate, an inhibitor for mast cell degranulation, suppresses skin fibrosis in Tsk (tight skin) mice, an animal model for scleroderma (*Am. J. Pathol.* 82, 493, 1976) (*J. Rheumatol.* 14, 299, 1987). Furthermore, it-has been reported that chymase activity is increased in Tsk mice (*Jp. J. Pharmacol.* 97 (sup. I) 60P, 1998), and that there is a correlation between the severity of the skin fibrosis and the number of skin mast cells in a bleomycin-induced scleroderma model in mice (*Clin. Immunol.* 92, 6, 1999). Regarding pulmonary fibrosis, in addition, it is known that pulmonary. fibrosis is not induced by administration of bleomycin in mast cell deficient mice, suggesting involvement of mast cells that produce chymase (*Agents Actions* 39, 20, 1993). Further, regarding hepatic fibrosis, the number of mast cells in human livers increases along with the fibrogenesis of livers (*J. Hepatol.* 26, 1042, 1997). A similar increase of mast cells is observed even in various hepatic fibrosis models (*Hepatology* 23, 888, 1996, *J. Hepatol.* 29, 112, 1998). In biliary cirrhosis model in rat, mast cell degranulation are observed in the liver, showing the involvement of mast cell granular components such as chymase in pathogenesis of fibrosis (*Hepatology* 23, 888, 1996). Regarding the involvement of chymase in fibrogenesis of the heart, on the other hand, it has been reported that chymase activity is 5-fold in the pressure-overloaded hamster heart in which fibrosis and apoptosis are observed (*FEBS lett.* 406, 301, 1997). Recently, it has been shown that rat mast cell chymase (RMCP-1) causes apoptosis of cardiomyocytes derived from neonatal rats, suggesting that chymase may play a role in cell death of cardiomyocytes and fibrogenesis during progression of heart failure (*Circulation* 100, 1443, 1999). Further, it has also been reported that the expression of mRNA of chymase is augmented in the end stage where fibrogenesis becomes prominent in a canine with heart failure induced by rapid right Ventricular pacing (Matsumoto et al., *73rd Scientific Sessions of American Heart Association,* November 2000, New Orleans, Abs. 2191). Restenosis following PTCA is a vascular disease associated with fibrosis. It has been reported that an increase in mast cells augmentation of expression of chymase is observed in balloon-injured artery in dog, and that tranilast that inhibits mast cell degranulation suppresses neointima formation in this model (*Circulation* 99, 1084, 1999). However, there is also a report that bleomycin induced pulmonary fibrosis is, induced even in mast cell-deficient mice in the same way as normal mice (*Lab. Invest.* 78, 1431, 1998). There are still many unclear points in the role of mast cells or chymase in various types of fibrosis.

There are findings suggesting the mechanism of action of chymase in fibrosis. For example, it has been reported that chymase promotes in culture the production of TGF-β, the major cytokine for fibrogenesis (*J. Biol. Chem.* 270, 4689, 1995). Further, there is a report that chymase acts in vitro on procollagen, a precursor of collagen, to promote collagen fibril formation (*J. Biol. Chem.* 272, 7127, 1997) and a report that chymase activates procollagenase (*Biochem. J.* 305, 301, 1995).

At the present time, a broad search is under way for substances which can inhibit chymase activity in animal models with the aim of elucidating the role of chymase in the body.

There are chymase inhibitors such as low molecular weight chymase inhibitors such as shown in print (*Protease Inhibitors;* Barrett et al., Eds; Elssevier Science B. V.;

Amsterdam, 1996), α-keto acid derivatives reported as peptide type inhibitors (WO93-25574, *Proc. Natl. Acad. Sci. USA*, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., *Biochemistry* 30, 485, 1991), peptide like inhibitors such as trifluoromethylketone derivatives (WO96-33974, Japanese Unexamined Patent Publication (Kokai) No. 10-53579) and acetoamide derivatives (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese Unexamined Patent Publication (Kokai) No. 10-245384), phenol ester derivatives (Japanese Unexamined Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc. have been reported, but no satisfactory medicament or treatment method using inhibition of the activity of chymase as a strategy for treatment has yet been established.

DISCLOSURE OF THE INVENTION

The object of the present invention is to provide a side effect-free, safe medicament for prevention or treatment of fibrosis of the skin or various organs, which suppresses the progression of the disease, prevents the progression of complications, and improves the quality of life of the patient.

The present inventors engaged in intensive studies to achieve this object focusing on subcutaneous fibrous layer hypertrophy involving the dysbolism of connective tissue protein and, as a result, found that a chymase inhibitor alleviates the dysbolism of collagen and suppresses the increase in the subcutaneous fibrous layer and thereby completed the present invention.

That is, in accordance with the present invention, there is provided a medicament for the prevention or treatment of fibrosis involving extracellular matrix dysbolism having a chymase inhibitor as an effective ingredient.

In accordance with the present invention, there is also provided a pharmaceutical composition for the prevention or treatment of fibrosis involving extracellular matrix dysbolism including an amount of a chymase inhibitor for alleviating extracellular matrix dysbolism and a pharmaceutically acceptable vehicle.

In accordance with the present invention, the present invention further provides a medicament for alleviating extracellular matrix dysbolism having a chymase inhibitor as an effective ingredient.

BEST MODE FOR CARRYING OUT THE INVENTION

Figure 1:
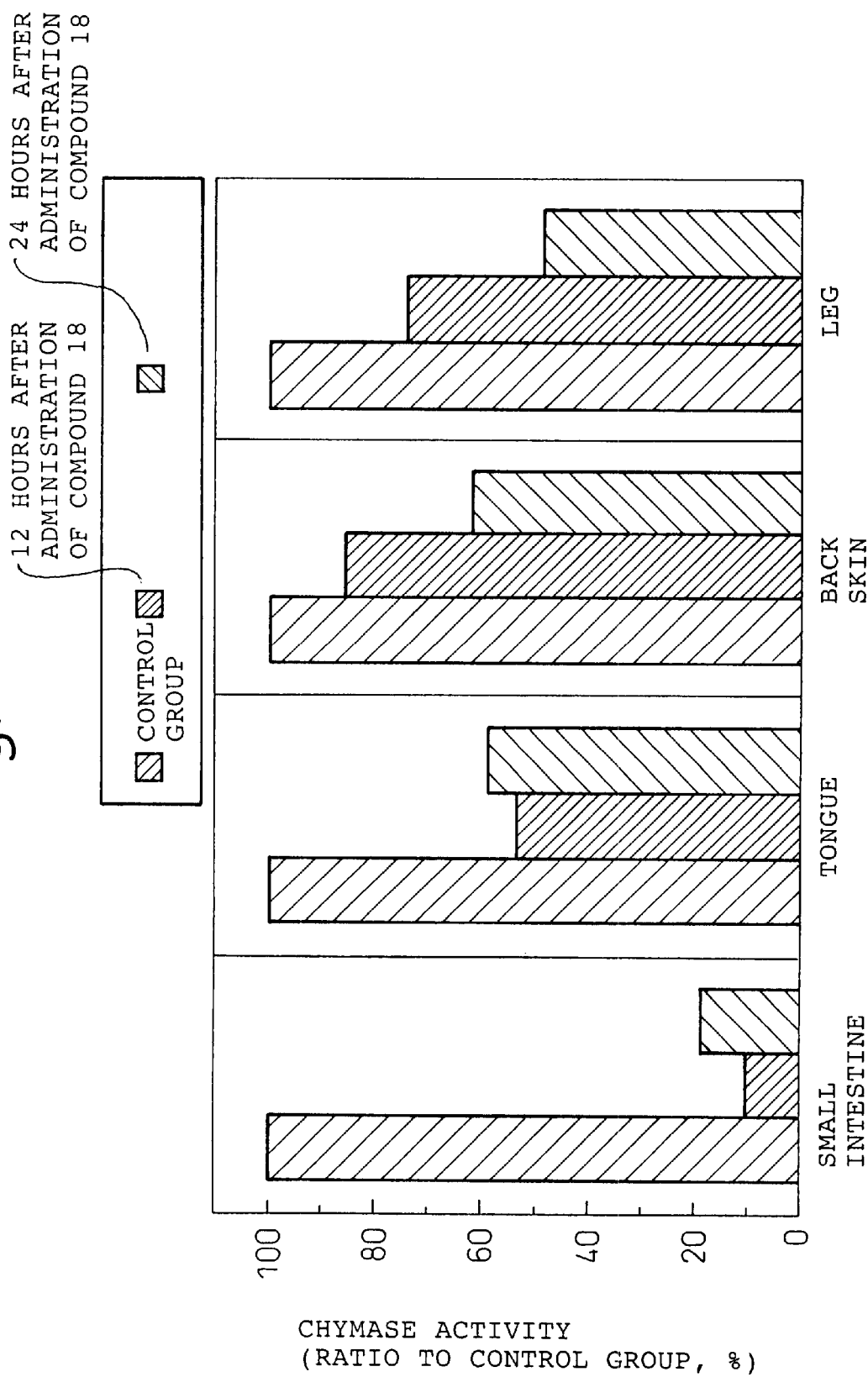
FIG. 1 is a graph showing the effects of a chymase inhibitor (Compound 18) on chymase activity in various tissues in mice in Example 2.

In this specification, the fibrosis involving extracellular matrix dysbolism includes diseases whose onset is caused by the occurrence of extracellular matrix dysbolism, diseases whose conditions are aggravated by the occurrence of extracellular matrix dysbolism, and diseases whose cure is delayed by the occurrence of extracellular matrix dysbolism. For example, these diseases include scleroderma, pulmonary fibrosis, benign prostatomegaly, myocardial fibrogenesis following myocardial infarction, myocardial fibrosis, musculoskeletal fibrosis, post-surgical adhesion, hypertropic scars and keloids, cirrhosis, hepatic fibrosis, renal fibrosis, fibrous vascular disorders, and complications of diabetes such as retinitis due to fibrous microvasculitis, neurosis, nephropathy, and peripheral arteritis or a condition related to the same.

The chymase inhibitor able to be used in the present invention can be selected as a substance inhibiting chymase activity by the use of methods workable by persons skilled in the art. As the method of selection, for example, the method of the later explained Example 1 may be used. The compounds obtained in this way include known compounds previously-reported as chymase inhibitors, for example, the low molecular weight chymase inhibitors such as shown in the book (*Protease Inhibitors;* Barrett et al., Eds; Elssevier Science B. V.; Amsterdam, 1996), α-keto acid derivatives reported as peptide type inhibitors (WO93-25574, *Proc.*

Natl. Acad. Sci. USA, 1995, 92, 6738), α,α-difluoro-β-keto acid derivatives (Japanese Unexamined Patent Publication (Kokai) No. 9-124691), tripeptide inhibitors (WO93-03625), phosphoric acid derivatives (Oleksyszyn et al., Biochemistry 30, 485, 1991), peptide like inhibitors such as trifluoromethylketone derivatives (WO96-33974, Japanese Unexamined Patent Publication (Kokai).No. 10-53579) and acetoamide derivatives (Japanese Unexamined Patent Publication (Kokai) No. 10-7661, Japanese Unexamined Patent Publication (Kokai) No. 10-53579, Japanese Unexamined Patent Publication (Kokai) No. 11-246437, WO99-41277, WO98-18794, WO96-39373), non-peptide type inhibitors such as triazine derivatives (Japanese Unexamined Patent Publication (Kokai) No. 8-208654 and Japanese Unexamined Patent Publication (Kokai) No. 10-245384), phenol ester derivatives (Japanese Unexamined. Patent Publication (Kokai) No. 10-87567), cephem derivatives (Japanese Unexamined Patent Publication (Kokai) No. 10-87493), isoxazole derivatives (Japanese Unexamined Patent Publication (Kokai) No. 11-1479), imidazolidine derivatives (WO96-04248), hydantoin derivatives (Japanese Unexamined Patent Publication (Kokai) No. 9-31061), quinazoline derivatives (WO97-11941), etc., but as a representative example of a preferable chymase inhibitor, a compound of the following formula (I) and its pharmaceutically acceptable salts may be mentioned.

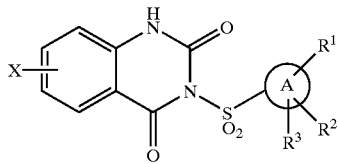

(I)

wherein, the ring A represents an aryl group;

$R^1$ represents a hydroxyl group, an amino group, a $C_1$ to $C_4$ lower alkylamino group which may be substituted with a carboxylic acid group, a $C_7$ to $C_{10}$ lower aralkylamino group which may be substituted with a carboxylic acid group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, a $C_1$ to $C_4$ lower alkyl group substituted with a carboxylic acid group, or a $C_2$ to $C_4$ lower alkylene group which may be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, or a carboxylic acid group or when the ring A is a benzene ring, $R^1$ and $R^2$ may form, together with the substituting benzene ring, a fused heterocyclic ring which may be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

In the general formula (I), preferable examples of the aryl group represented by the ring A are a benzene ring and a naphthalene ring.

Preferable examples of the $C_1$ to $C_4$ lower alkylamino group which may be substituted with the carboxylic acid group and the $C_7$ to $C_{12}$ lower aralkylamino group which may be substituted with a carboxylic acid group represented by $R^1$ are a methylamino group, an ethylamino group, a propylamino group, a butylamino group, a carboxymethylamino group, a carboxyethylamino group, a carboxypropylamino group, a carboxybutylamino group, a benzylamino group, a phenetylamino group, a phenylpropylamino group, a phenylbutylamino group, a carboxybenzylamino group, a carboxyphenetylamino group, a carboxyphenylpropylamino group, a carboxyphenylbutylamino group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the $C_1$ to $C_4$ lower alkyl group substituted with a carboxylic acid group represented by $R^1$ are an acetic acid group, a propionic acid group, a butyric acid group, a valeric acid group, etc.

Preferable examples of the $C_2$ to $C_4$ lower alkylene group substituted with a carboxylic acid group represented by $R^1$ are an acrylic acid group, a crotonic acid group, etc.

Preferable examples of the unsubstituted or substituted $C_1$ to $C_4$ lower alkyl group represented by $R^2$ or $R^3$ are a straight-chain alkyl group such as a methyl group, an ethyl group, a n-propyl group, and a n-butyl group and a branched alkyl group such as an isopropyl group, a sec-butyl group, and a t-butyl group.

Preferable examples of the substituent group of the $C_1$ to $C_4$ lower alkyl group are a carboxylic acid group, a halogen atom such as a fluorine atom and a chlorine atom, a $C_1$ to $C_4$ lower alkoxy group, an amino group, a methylamino group, a dimethylamino group, a carboxymethylamino group, a carboxyethylamino group, etc.

Preferable examples of the halogen atom represented by $R^2$ or $R^3$ are a fluorine atom, a chlorine atom, a bromine atom and an iodine atom.

Preferable examples of the $C_1$ to $C_4$ lower alkoxyl group represented by $R^2$ or $R^3$ are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the unsubstituted or substituted $C_1$ to $C_4$ lower alkylamino group represented by $R^2$ or $R^3$ are a methylamino group, an ethylamino group, a propylamino group, a butylamino group, etc.

Preferable examples of the substituent group of the $C_1$ to $C_4$ lower alkylamino group are a carboxylic acid group, a halogen atom such as a fluorine atom and a chlorine atom, a $C_1$ to $C_4$ lower alkoxyl group, etc.

Preferable examples of the unsubstituted or substituted $C_7$ to $C_{12}$ lower aralkylamino group represented by $R^2$ or $R^3$ are a benzylamino group, a phenetylamino group, a phenylpropylamino group, a phenylbutylamino group, etc.

Preferable examples of the substituent group of the aralkylamino group are a carboxylic acid group, a halogen atom such as a fluorine atom and a chlorine atom, a $C_1$ to $C_4$ lower alkoxyl group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples, of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the fused heterocyclic ring which may be substituted with a carboxylic acid and in which the carbon atom in the ring may form a carbonyl group which $R^1$ and $R^2$ form together with the substituting benzene ring when the ring A is a benzene ring, are a tetrahydroquinoline ring and a benzoxazine ring, for example, a tetrahydroquinoline, a benzoxazine, a quinoxaline, a benzodioxane, a carboxytetrahydroquinoline, a carboxybenzoxazine, a carboxyquinoxaline, a carboxybenzodioxane, etc.

Preferable examples of the $C_1$ to $C_4$ lower alkyl group represented by X are a straight-chain alkyl group such as a methyl group, an ethyl group, a n-propyl group, and a n-butyl group and a branched alkyl group such as an isopropyl group, a sec-butyl group, and a t-butyl group.

Preferable examples of the $C_1$ to $C_4$ lower alkoxyl group represented by X are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the halogen atom represented by X, are a fluorine atom, a chlorine atom, a bromine atom and an iodine atom.

Further, examples of a pharmaceutically acceptable salts are an acid salt such as a hydrochloric acid salt, a methanesulfonic acid salt, and a trifluoroacetic acid salt and an alkali metal salt such as a sodium salt and a potassium salt.

The quinazoline derivative having the formula (I) according to the present invention may, for example, be synthesized by the following Synthesis Method (A) or (B).

Synthesis Method (A)

A compound having the formula (I-1):

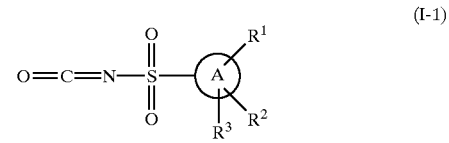

(I-1)

wherein the ring A is the same as defined above and $R^{1'}$, $R^{2'}$ and $R^{3'}$ represent $R^1$, $R^2$ and $R^3$, which may be protected with a protecting group, respectively, and $R^1$, $R^2$ and $R^3$ represent the same as defined above is reacted with an anthranilic acid derivative having the formula (I-2):

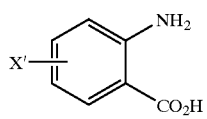

(I-2)

wherein X' represents X, which may be protected with a protecting group, and X represents the same as defined above using the method described, for example, in JP-A-6-199839 to obtain a sulfonylurea derivative having the formula (I-3):

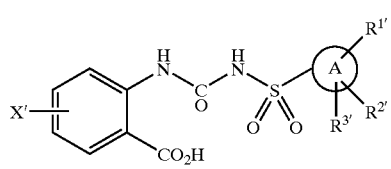

(I-3)

wherein the ring A, $R^{1'}$, $R^{2'}$, $R^{3'}$ and X' represent the same as defined above, then, a condensing agent for example, 1,1'-carbonyldiimidazole (hereinafter referred to as CDI) is used to obtain the quinazoline ring, and if necessary, the protecting groups of $R^1$, $R^2$, $R^3$ and X are deprotected.

In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

The compound having the formula (I-1) used in this reaction includes a commercially available or known compound or a compound which can be synthesized by a known method may be used. For example, using the synthesis method described in the specification of European Patent No. 0269141, it is possible to use a compound which can be synthesized from the corresponding sulfonamide derivative using chlorosulfonyl isocyanate. For example, it is possible to use 3-allyloxycarbonylmethylbenzenesulfonyl isocyanate, 4-allyloxycarbonylmethylbenzenesulfonyl isocyanate, 4-allyloxybenzenesulfonyl isocyanate, etc.

As the anthranilic acid derivative having the formula (I-2) used for this reaction, a commercially available or known compound or a compound which can be synthesized by a known method may be used. For example, anthranilic acid, 4-chloroanthranilic acid, 4-methoxyanthranilic acid, 5-chloroanthranilic acid, 4-hydroxyanthranilic acid, etc. may be used.

The reaction to obtain the quinazoline ring from the sulfonylurea derivative having the formula (I-3) may be carried out using an aprotonic solvent such as, for example, an ether solvent such as tetrahydrofuran and dioxane, a halogen-containing solvent such as methylene chloride, or dimethylformamide etc. at a temperature of −50° C. to 50° C., preferably −20° C. to room temperature. Further, for the cyclization reaction, it is possible to use an ordinary condensing agent which includes, for example, CDI, dicyclohexylcarbodiimide, and similar carbodiimide compounds, mixed anhydrides, etc. The deprotecting reaction can be carried out by an ordinary method using hydrolysis with an acid or alkali, reduction or oxidation etc.

Synthesis Method (B)

A compound having the formula (I-4):

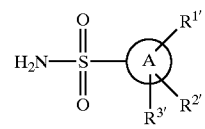

(I-4)

wherein the ring A, $R^{1'}$, $R^{2'}$ and $R^{3'}$ represent the same as defined above is condensed with an anthranilic acid derivative having the formula (I-5):

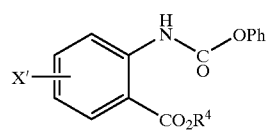

(I-5)

wherein X' represents the same as defined above, Ph represents a phenyl group, and $R^4$ represents a protecting group of the carboxyl group, which is specifically a group capable of being released by hydrolysis or hydrogenolysis, such as, for example, a methyl group, an ethyl group, or a benzyl group using, for example, 1,8-diazabicyclo[5,4,0]-7-undecene (hereinafter referred to as DBU) to form a sulfonylurea derivative having the formula (I-6):

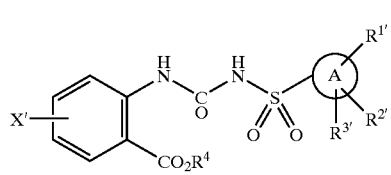

(I-6)

wherein the ring A, $R^{1'}$, $R^{2'}$, $R^{3'}$, $R^4$ and X' are the same as defined above, which is then hydrolyzed with an alkali or hydrogenolyzed to derive a corresponding carboxylic acid represented by the formula (I-3), then the quinazoline ring is obtained and optionally the protecting groups of $R^1$, $R^2$, $R^3$ and X are deprotected, in the same way as in Synthesis Method (A). In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

As the compound having the formula (I-4) used in the reaction, a commercially available or known compound or a compound which can be synthesized by a known method may be used. For example, 3-hydroxybenzenesulfonamide, 2-aminobenzenesulfonamide, 3-aminobenzenesulfonamide, 4-aminobenzenesulfonamide, (±)-2-(4-aminosulfonylphenyl)butyric acid, 3-benzyloxycarbonylamino-4-chlorobenzenesulfonamide 4-benzyloxycarbonylamino-3-chlorobenzenesulfonamide, 4-amino-3,5-dichlorobenzenesulfonamide, 3-benzyloxycarbonylamino-4-methylbenzenesulfonamide, 4-t-butoxycarbonyl-3-hydroxybenzenesulfonamide, 3-benzyloxycarbonylamino-4-t-butoxycarbonylbenzenesulfonamide, 4-t-butoxycarbonyl-3-hydroxybenzenesulfonamide, 3-t-butoxycarbonyl-4-hydroxybenzenesulfonamide, 3-acetamide-4-methoxybenzenesulfonamide, 3-(3-aminosulfonyl) phenylacrylic acid t-butylester, 3-amino-4-methoxybenzenesulfonamide, 4-methoxy-3-methylsulfonylaminobenzenesulfonamide, 3-carboxy-4hydroxy-2-naphthalenesulfonamide, 4-benzyloxycarbonylamino-3-t-butoxycarbonylbenzenesulfonamide, (±)-3-t-butoxycarbonyl-2-oxo-1H,3H-quinoline-7-sulfonamide, (±)-2-t-butoxycarbonyl-3-oxo-1,4-benzoxazine-6-sulfonamide, etc. may be used.

As the anthranilic acid derivative having the formula (I-5) used in this reaction, a commercially available or known compound or a compound which can be synthesized by a known method may be used. For example, methyl 4-chloro-2-N-phenoxycarbonylanthranilate, ethyl 4-chloro-2-N-phenoxycarbonylanthranilate, benzyl 4-chloro-2-N-phenoxycarbonylanthranilate, methyl 5-chloro-2-N-phenoxycarbonylanthranilate, ethyl 5-chloro-2-N-phenoxycarbonylanthranilate, benzyl 5-chloro-2-N-phenoxycarbonylanthranilate, methyl 4-methoxy-2-N-phenoxycarbonylanthranilate, ethyl 4-methoxy-2-N-phenoxycarbonylanthranilate, benzyl 4-methoxy-2-N-phenoxycarbonylanthranilate, methyl 4-hydroxy-2-N-phenoxycarbonylanthranilate, ethyl 4-hydroxy-2-N-phenoxycarbonylanthranilate, benzyl 4-hydroxy-2-N-phenoxycarbonylanthranilate, etc. may be used.

The reaction for obtaining the compound having the formula (I-4) and the anthranilic acid derivative having the formula (I-5) condense to obtain a sulfonylurea derivative having the formula (I-6), may be carried out using an aprotic solvent, for example, an ether solvent such as tetrahydrofuran or dioxane, a halogen-containing solvent such as methylene chloride, or dimethylformamide etc. at a temperature of −50° C. to 50° C., preferably −20° C. to room temperature. Further, as the usable for the condensation reaction, an organic strong base such as DBU, inorganic bases such as potassium carbonate, sodium carbonate, potassium hydroxide, and sodium hydroxide, or metal bases such as sodium hydride may be used.

In the reaction for alkali hydrolysis or hydrogenolysis of the sulfonylurea derivative having the formula (I-6) thus obtained to obtain the sulfonylurea derivative having the formula (I-3), ordinary hydrolysis conditions or hydrogenolysis conditions for esters may be used.

Note that the above reaction may be carried out while protecting the functional groups not involved in the reaction. According to the type of the protecting group, the protection is removed by chemical reduction or other ordinary protection-removing reactions. For example, when the protecting group is a t-butyl group or t-butoxycarbonyl group, trifluoroacetic acid may be used, while when it is an allyl group, palladium catalysts such as tetrakis (triphenylphosphine)palladium (0) may be used.

The compound having the formula (I), wherein $R^1$ represents an amino group acylated with a $C_1$ to $C_4$ lower aliphatic acid which may be substituted with a carboxylic acid, an amino group acylated with an aromatic ring carboxylic acid which may be substituted with a carboxylic acid and an amino group acylated with an heteroaromatic ring carboxylic acid which may be substituted with a carboxylic acid, can be obtained from the compound having the formula (I), wherein $R^1$ represents an amino group, by acylating the same with carboxylic acid, carboxylic acid chloride, carboxylic acid anhydride using an ordinary method.

The compound having the formula (I), wherein $R^1$ represents an amino group sulfonylated with a $C_1$ to $C_4$ lower alkane sulfonic acid which may be substituted with a carboxylic acid, an amino group sulfonylated with an aromatic ring sulfonic acid which may be substituted with a carboxylic acid and an amino group sulfonylated with an heteroaromatic ring sulfonic acid which may be substituted with a carboxylic acid, can be obtained from the compound having the formula (I), wherein $R^1$ represents an amino group, by sulfonylating the same with sulfonic acid or sulfonic acid chloride using an ordinary method.

The product obtained according to the above-mentioned processes can be purified by a method such as recrystallization or column chromatography.

If necessary, the compounds having the formula (I) of the present invention obtained according to the above-mentioned processes can each be reacted with one of various acids or basis to convert the compound into their salt. Exemplary acids usable for the conversion of the compound having the formula (I) into their salts can include inorganic acids such as hydrochloric acid, hydrobromic acid, nitric acid, sulfuric acid, phosphoric acid; and organic acids such as methanesulfonic acid, benzenesulfonic acid, p-toluenesulfonic acid, trifluoroacetic acid, citric acid, lactic acid, maleic acid, fumaric acid, tartaric acid, acetic acid, adipic acid, palmitic acid and tannic acid. Exemplary usable basis for the conversion of the compound having the formula (I) into their salts can include sodium hydroxide, lithium hydroxide and potassium hydroxide.

Further, the compounds having the formula (I) according to the present invention include those containing asymmetric centers. Each racemic mixture can be isolated by one or more of various methods, whereby a single optically-active substance can be obtained. Usable methods include, for example:

(1) Isolation by optically active column.
(2) Isolation by recrystallization subsequent to conversion into a salt with an optically active acid or base.
(3) Isolation by a combination of the above methods (1) and (2).

These compounds can be evaluated according to the method of Example 4 or 7 below, with respect to the improvement in the abnormal exacerbation.

To use the effective ingredient of the present invention as a medicament for the prevention or treatment of fibrosis involving extracellular matrix dysbolism, a pharmaceutical composition for the prevention or treatment of fibrosis involving extra cellular matrix dysbolism, and a medicament for alleviation of extracellular matrix dysbolism, one or more of the compounds of the present invention may be mixed and formed into a form suitable for use in the method of administration by an ordinary method. Examples of preparation forms for oral administration include capsules, tablets, granules, fine granules, syrups, dry syrups, and other preparations, while examples of preparation forms for non-oral administration include injections and besides suppositories such as rectal suppositories and vaginal suppositories, transnasal preparations such as sprays and ointments, and percutaneous preparations such as tapes for percutaneous absorption.

The clinical dose of the compound according to the present invention varies according to the diseased condition, degree of seriousness, age, presence of complications, etc.

and also varies according to its preparation form. In the case of oral administration, however, it may be dosed usually, in terms of effective ingredients, as 1 to 1000 mg per adult per day. In the case of non-oral administration, it is sufficient to administer 1/10 to 1/2 the amount of the case of oral administration. These dosages can be suitably adjusted according to the age, the diseased condition, and the like of the patient to be dosed.

In the present invention, the chymase inhibitor can be administered alone as it is without being mixed with another effective ingredient, but considering the disease in question, the symptoms, complications, etc., it may also administered as a medicinal preparation containing other effective ingredients. Further, it may also be combined with these other effective ingredients. The amounts of the other effective ingredients used are not particularly limited, but are determined considering the minimum amounts for expression of their effects alone, the occurrence of side effects, etc.

In treatment, the form of preparation and the method of combined treatment including preparations containing the chymase inhibitor alone as an effective ingredient and preparations also containing other effective ingredients are suitably selected by a physician in accordance with the age of the patient, the symptoms, etc.

The toxicity of the compound according to the present invention is low. The acute toxicity values $LD_{50}$ at 24 hours after oral administration to 5-week old male mice were 1 g/kg or more.

EXAMPLES

The present invention will now be further explained by, but is by no means limited to, the following Examples, but the scope of the invention is not limited to these Examples needless to say.

To demonstrate the usefulness of the chymase inhibitor against fibrosis, the test results obtained by using Tsk mice, as the model of sclerodermatous mice, and bleomycin-induced mice fibrosis in lung, as the model of fibrosis, are provided below.

Preparation Example 1

Synthesis of 7-chloro-3-(3-hydroxybenzenesulfonyl)-2,4(1H,3H)-quinazolinedione (Compound 1)

Following the Synthesis Method (B), 938 mg (5.42 mmol) of 3-hydroxybenzenesulfonamide was dissolved in 40 ml of tetrahydrofuran, then 892 μl (5.96 mmol) of 1,8-diazabicyclo[5,4,0]-7-undecene (hereinafter referred to as DBU) was added dropwise. The reaction solution was stirred at room temperature for 15 minutes, then 1.66 g (5.42 mmol) of methyl 4-chloro-2-N-phenoxycarbonylanthranilate was added and the mixture was stirred at room temperature overnight. An excess amount of water was poured into the reaction solution, then the mixture was made acidic with hydrochloric acid and extracted with ethyl acetate. The organic layer was washed with water and saturated saline, dried over anhydrous magnesium sulfate, and concentrated. The crude product thus obtained was purified by silica gel column chromatography (0% to 5% methanol/dichloromethane) to obtain 1.23 g (yield 59%) of methyl 4-chloro-2-{[(3-hydroxybenzenesulfonylamino)carbonyl]amino} benzoate. Properties: colorless amorphous, PMR (δ ppm, DMSO-$d_6$): 3.91 (3H, s), 7.02 (1H, m), 7.09 (1H, m), 7.34 (1H, t), 7.57 (2H, m), 7.89 (1H, d), 8.38 (1H, d), 10.94 (1H, s). Next, the 1.23 g (3.2 mmol) of the compound thus obtained was dissolved in 20 ml of methanol, then 10 ml of 2N sodium hydroxide aqueous solution was added dropwise. The reaction solution was stirred at room temperature for 15 minutes, then an excess amount of water was added and the mixture was made acidic with hydrochloric acid. This was then stirred to cause crystals to precipitate which were then obtained by filtration and dried to obtain carboxylic acid. The product thus obtained was dissolved in 50 ml of tetrahydrofuran (hereinafter referred to as THF), then 434 mg (2.68 mmol) of CDI was added under ice cooling and the mixture was stirred for 30 minutes. The reaction solution was diluted with ethyl acetate, washed with water and saturated saline, and dried over anhydrous magnesium sulfate, then concentrated to obtain a crude product. The crude product was purified by silica gel column chromatography (ethyl acetate:n-hexane=1:2) to obtain 230 mg (yield 20%: 2 steps) of the above-identified compound. Properties: colorless crystal, Melting point: >200° C. (decomposition), PMR (δ ppm, DMSO-$d_6$): 7.12 (2H, s), 7.24 (1H, d), 7.48 (1H, t), 7.58 (2H, s), 7.85 (1H, d), 10.28 (1H, s), 11.63 (1H, s).

Preparation Example 2

Synthesis of 3-(2-aminobenzenesulfonyl)-7-chloro-2,4(1H,3H)-quinazolinedione (Compound 2)

2.7 g (15.7 mmol) of 2-aminobenzenesulfonamide and 4.8 g (15.7 mmol) of methyl 4-chloro-2-N-phenoxycarbonylanthranilate were treated in the same way as Preparation Example 1 to obtain 3.2 g (yield 58%: 3 steps) of the above-identified compound. Properties: colorless crystal, Melting point: >200° C. (decomposition), PMR (δ ppm, DMSO-$d_6$): 6.46 (2H, s), 6.65 (1H, t), 6.81 (1H, d), 7.12 (1H, s), 7.23 (1H, d), 7.34 (1H, t), 7.76 (1H, d), 7.86 (1H, d).

Preparation Example 3

Synthesis of 7-chloro-3-(2-methylsulfonylaminobenzenesulfonyl)-2,4(1H,3H)-quinazolinedione (Compound 3)

22 mg (0.06 mmol) of Compound 2 was dissolved in 200 μl of pyridine, 11.6 μl (0.15 mmol) of methanesulfonyl chloride was added dropwise, then the resultant mixture was stirred at room temperature overnight. An excess amount of water was added to the reaction solution and the mixture was extracted with ethyl acetate. The organic layer was washed with 1N aqueous hydrochloric acid solution and saturated saline, then dried over anhydrous magnesium sulfate and concentrated to obtain a crude product. The crude product was crystallized from diethyl ether to obtain 16 mg (0.04 mmol) of the above-identified compound. Properties: colorless crystal, Melting point: >200° C. (decomposition), PMR (δ ppm, DMSO-$d_6$): 3.61 (3H, s), 7.10 (1H, d), 7.20 (1H, d), 7.74 (1H, d), 7.82–7.90 (4H, m), 8.34 (1H, d), 11.70 (1H, s).

Preparation Example 4

Synthesis of 3-(4-aminobenzenesulfonyl)-7-chloro-2,4(1H,3H)-quinazolinedione (Compound 4)

2.7 g (15.7 mmol) of 4-aminobenzenesulfonamide and 4.8 g (15.7 mmol) of methyl 4-chloro-2-N-phenoxycarbonylanthranilate were treated in the same way as Preparation Example 1 to obtain 7.9 g (yield 94%) of methyl 2-{[(4-aminobenzenesulfonylamino)carbonyl]amino}-4-chlorobenzoate. Properties: colorless amorphous, PMR (δ ppm, DMSO-d$_6$): 33.59 (3H, s), 5.37 (2H, s), 6.45 (2H, d), 6.83 (1H, dd), 7.41 (2H, d), 7.81,(1H, d), 8.66 (1H, d), 9.64 (1H, s).

Then, from the resultant 7.9 g (14.8 mmol) of sulfonylurea product, in the same way, 4.3 g (yield 83%: 2 steps) of the above-identified compound was obtained. Properties: colorless crystal, Melting point: >200° C. (decomposition), PMR (δ ppm, DMSO-d$_6$): 6.39 (2H, s), 6.63 (2H, d), 7.09 (1H, s), 7.22 (1H, d), 7.76 (2H, d), 7.83 (1H, d), 11.51 (1H, s).

Preparation Example 5

Synthesis of 3-(3-carboxymethyl-benzenesulfonyl)-7-chloro-2,4(1H,3H)-quinazolinedione (Compound 5)

Following the Synthesis Method (A), 3.27 g (11.6 mmol) of 3-allyloxycarbonylmethylbenzenesulfonyl isocyanate was dissolved in 100 ml of anhydrous THF, then 1.98 g. (11.5 mmol) of 4-chloroanthranilic acid was added and the mixture was stirred at room temperature for 2 hours. The reaction solution was cooled with ice water, then 1.87 g (11.5 mmol) of CDI was added and the resultant mixture was stirred under ice cooling for 30 minutes. An excess amount of water was poured into the reaction solution, then the mixture was extracted with ethyl acetate. The organic layer was washed, dried, and concentrated to obtain a crude product. This was crystallized with a small amount of ethyl acetate to obtain 2.0 g (yield 40%) of 3-(3allyloxycarbonylmethylbenzenesulfonyl)-7-chloro-2,4 (1H,3H)-quinazolinedione. The allyl product thus obtained was dissolved in 100 ml of a formic acid-THF (1:9) mixture and 700 mg of triphenylphosphine was added. The reactor was shaded from light and under nitrogen atmosphere, then 700 mg of tetrakis(triphenylphosphine)palladium (0) was added and the resultant mixture was stirred while shaded at room temperature overnight. The reaction solution was concentrated in vacuo and the solid obtained was washed with methylene chloride to obtain 1.47 g (yield 81%) of the above-identified compound. Properties: colorless crystal, Melting point: >200° C. (decomposition), PMR (δ ppm, DMSO-d$_6$): 3.76 (2H, s), 7.13 (1H, s), 7.24 (1H, d), 7.61–7.69 (2H, m), 7.86 (1H, d), 8.05 (1H, s), 12.50 (1H, br).

Preparation Example 6

Synthesis of 3-(4-carboxymethyl-benzenesulfonyl)-7-chloro-2,4(1H,3H)-quinazolinedione (Compound 6)

1.10 g (3.95 mmol) of 4-allyloxycarbonylmethylbenzenesulfonyl isocyanate and 678 mg (3.95 mmol) of 4-chloroanthranilic acid were treated in the same way as in Preparation Example 5 to obtain 657 mg (yield 38%) of 3-(4-allyloxycarbonylbenzenesulfonyl)-7-chloro-2,4(1H,3H)-quinazolinedione. 538 mg (1.24 mmol) thereof was treated in the same way to obtain 342 mg of the above-identified compound (yield 70%). Properties: colorless crystal, Melting point: >200° C. (decomposition), PMR (δ ppm, DMSO-d$_6$): 3.75 (2H, s), 7.13 (1H, s), 7.23 (1H, d), 7.61–7.69 (2H, m), 7.86 (1H, d), 8.05 (2H, s), 12.07 (2H, br).

Preparation Example 7

Synthesis of (±)-2-{4-[(7-chloro-2,4(1H,3H)-quinazolin-3-yl)sulfonyl]phenyl}butyric acid (compound 7)

1.02 g (3.41 mmol) of t-butyl (±)-2-(4-aminosulfonylphenyl)butyrate acid and 1.04 g (3.41 mmol) of methyl 4-chloro-2-N-phenoxycarbonylanthranilate were treated in the same way as Preparation Example 1 to obtain 1.46 g (yield 84%) of methyl 2-[({4-[1-(t-butoxycarbonyl)propyl]benzenesulfonylamino}carbonyl)amino ]-4-chlorobenzoate. Properties: colorless amorphous, PMR (δ ppm, CDCl$_3$): 0.89 (3H, t), 1.38 (9H, s), 1.69–1.76 (1H, m), 2.03–2.10 (1H, m), 3.42 (1H, t), 3.94 (3H, s), 7.04 (1H, d), 7.47 (2H, d), 7.93 (1H, d), 8.01 (2H, d), 8.45 (1H, br), 11.04 (1H, br).

Next, 4.3 ml (8.6 mmol) of 2N sodium hydroxide aqueous solution was used to similarly form carboxylic acid in an amount of 1.43 g and 463 mg (2.86 mmol) of CDI was used to obtain 970 mg (yield 71%: 2 steps) of t-butyl (±)-2-{4-[(7-chloro-2,4(1H,3H)-quinazolin-3-yl)sulfonyl]phenyl}butyrate.

Further, the t-butylester thus obtained was dissolved in 5 ml of dichloromethane, then 5 ml of trifluoroacetic acid was added and the resultant mixture was stirred at room temperature for 40 minutes. The reaction solution was concentrated in vacuo and the resultant crude product was washed with a small amount of diethyl ether to obtain 820 mg of the above-identified compound (yield 96%). Properties: colorless crystal, Melting point: >200° C. (decomposition), PMR (δ ppm, DMSO-d$_6$): 0.84 (3H, t), 1.67–1.75 (1H, m), 1.98–2.05 (1H, m), 3.62 (1H, t), 7.11 (1H, s), 7.24 (1H, d), 7.61 (2H, d), 7.86 (1H, d), 8.13 (2H, d), 11.62 (1H, s).

Preparation Example 8

Synthesis of 3-(3-amino-4-chlorobenzenesulfonyl)-7-chloro-2,4(1H,3H)-quinazolinedione (Compound 8)

1.0 g (2.93 mmol) of 3-benzyloxycarbonylamino-4-chlorobenzenesulfonamide and 1.18 g (2.93 mmol) of benzyl 4-chloro-2-N-phenoxycarbonylanthranilate were treated in the same way as Preparation Example 1 to obtain 1.43 g (yield 78%) of benzyl 2-{[(3-benzyloxycarbonylamino-4-chlorobenzene sulfonylamino)carbonyl]amino}-4-chlorobenzoate. Properties: colorless amorphous, PMR (δ ppm, DMSO-d$_6$): 5.19 (2H, s), 5.36 (2H, s), 7.21 (1H, dd), 7.34–7.48 (10H, m), 7.72–7.76 (2H, m), 7.97 (1H, d), 8.25 (1H, d), 8.30 (1H, d), 9.53 (1H, s), 10.30 (1H, s). 1.38 g (2.20 mmol) thereof was dissolved in 50ml of THF, then 200 mg of palladium-carbon (10%) was added and the mixture was stirred under a hydrogen flow for 2 hours. The reaction mixture was filtered with Celite to remove the palladium-carbon, then the filtrate was concentrated in vacuo to obtain a carboxylic acid. The product obtained was suspended in 50 ml of THF, then 356 mg (2.20 mmol) of CDI was added under ice cooling and the resultant mixture was treated in the same way as Preparation Example 1 to obtain 560 mg (yield 66%: 2 steps) of the above-identified compound. Properties: colorless crystal, Melting point: >200° C. (decomposition), PMR (δ ppm, DMSO-d$_6$): 6.00 (2H, s), 7.12 (1H, s), 7.26 (2H, t), 7.48 (1H, d), 7.66 (1H, s), 7.86 (1H, d), 11.76 (1H, br).

Preparation Example 9

Synthesis of 3-(4-amino-3,5-dichlorobenzenesulfonyl)-7-chloro-2,4(1H,3H)-quinazolinedione (Compound 9)

1.06 g (4.40 mmol) of 4-amino-3,5-dichlorobenzenesulfonamide and 1.34 g (4.40 mmol) of methyl 4-chloro-2-N-phenoxycarbonylanthranilate were treated in the same way as Preparation Example 1 to obtain 905 mg (yield 44%) of methyl 2-{[(4-amino-3,5-dichlorobenzenesulfonylamino)carbonyl]amino}-4-chlorobenzoate. Properties: colorless amorphous, PMR (δ ppm, DMSO-$d_6$): 3.87 (3H, s), 6.59 (2H, br), 7.22 (1H, dd), 7.72 (2H, s), 7.93 (1H, d), 8.24 (1H, d), 10.17 (1H, s).

Then, from 905 mg (2.0 mmol) of the resultant sulfonylurea product, in the same way, 660 mg (yield 82%: 2 steps) of the above-identified compound was obtained. Properties: colorless crystal, Melting point: >200° C. (decomposition), PMR (δ ppm, DMSO-$d_6$): 6.80 (2H, s), 7.12 (1H, s), 7.24 (1H, d), 7.86 (1H, d), 7.92 (2H, s), 11.63 (1H, br).

Preparation Example 10

Synthesis of 3-(3-amino-4-methylbenzenesulfonyl)-7-chloro-2,4(1H,3H)-quinazolinedione (Compound 10)

960 mg (3.00 mmol) of 3-benzyloxycarbonylamino-4-methylbenzenesulfonamide and 1.14 g (3.00 mmol) of benzyl 4-chloro-2-N-phenoxycarbonylanthranilate were treated in the same way as in Preparation Example 8 to obtain 1.14 g (yield 62% of benzyl 2-{[(3-benzyloxycarbonylamino-4-methylbenzenesulfonylamino)carbonyl]amino}-4-chlorobenzoate. Properties: colorless amorphous, PMR (δ ppm, DMSO-$d_6$): 2.30 (3H, s), 5.17 (2H, s), 5.36 (2H, s), 7.20 (1H, dd), 7.33–7.48 (11H, m), 7.63 (1H, d), 7.97 (1H, d), 8.11 (1H, s), 8.25 (1H, s), 9.27 (1H, s), 10.30 (1H, s), 12.20 (1H, br).

Then, from 1.14 g (1.87 mmol) of the resultant sulfonylurea product, in the same way, 190 mg (yield 27%: 2 steps) of the above-identified compound was obtained. Properties: colorless crystal, Melting point: >200° C. (decomposition), PMR (δ ppm, DMSO-$d_6$): 2.12 (3H, s), 5.47 (2H, s), 7.12 (1H, s), 7.16–7.25 (3H, m), 7.38 (1H, s), 7.85 (1H, d), 11.58 (1H, s).

Preparation Example 11

Synthesis of 3-[(3-carboxymethylaminophenyl)sulfonyl]-7-chloro-2,4(1H,3H)-quinazolinedione (Compound 11)

1.62 g (5.65 mmol) of 3-t-butoxycarbonylmethylaminobenzenesulfonamide and 1.73 g (5.65 mmol) of methyl 4-chloro-2-N-phenoxycarbonylanthranilate were treated in the same way as in Preparation Example 7 to obtain 209 mg (yield 9%: 4 steps) of the above-identified compound. Properties: colorless crystal, Melting point: >200° C. (decomposition), PMR (δ ppm, DMSO-$d_6$): 3.86 (2H, s), 6.88 (1H, s), 7.12 (1H, s), 7.24 (1H, d), 7.30–7.38 (3H, m), 7.86 (1H, d), 11.61 (1H, br).

Preparation Example 12

Synthesis of 3-(3-aminobenzenesulfonyl)-7-chloro-2,4(1H,3H)-quinazolinedione (Compound 12)

3.5 g (12.9 mmol) of 3-t-butoxycarbonylaminobenzenesulfonamide and 3.9 g (12.8 mmol) of methyl 4-chloro-2-N-phenoxycarbonylanthranilate were treated in the same way as in Preparation Example 7 to obtain 2.2 g (yield 49%: 4 steps) of the above-identified compound. Properties: colorless crystal, Melting point: >200° C. (decomposition), PMR (δ ppm, DMSO-$d_6$): 5.72 (2H, s), 6.87 (1H, d), 7.12 (1H, s), 7.23–7.27 (2H, m), 7.33 (1H, s), 7.86 (1H, d), 11.61 (1H, s).

Preparation Example 13

Synthesis of 2-{3-[(7-chloro-2,4(1H,3H)-quinazolinedion-3-yl)sulfonyl]phenylaminocarbonyl}propionic acid (Compound 13)

100 mg (0.28 mmol) of Compound 12 was dissolved in 5 ml of THF, 100 mg (1.0 mmol) of succinic anhydride was added, and the resultant mixture was heated and refluxed for 3 hours. The reaction solution was concentrated in vacuo and the crude product thus obtained was crystallized with ethyl acetate-diethyl ether to obtain 120 mg (yield 96%) of the above-identified compound. Properties: colorless crystal, Melting point: 187–188° C., PMR (δ ppm, DMSO-$d_6$): 2.54 (2H, d), 2.59 (2H, d), 7.12 (1H, s), 7.24 (1H, d), 7.59 (1H, t), 7.80 (1H, d), 7.86 (1H, d), 7.96 (1H, d), 8.41 (1H, s), 10.40 (1H, s), 11.63 (1H, br), 12.10 (1H, br).

Preparation Example 14

Synthesis of 3-{3-[(7-chloro-2,4(1H,3H)-quinazolinedion-3-yl)sulfonyl]phenyl}acrylic acid (Compound 14)

1.54 g (5.44 mmol) of t-butyl 3-(3-aminosulfonyl)phenylacrylate and 1.66 g (5.44 mmol) of methyl 4-chloro-2-N-phenoxycarbonylanthranilate were treated in the same way as in Preparation Example 7 to obtain 2.18 g (yield 81%) of methyl 2-({[3-(3-t-butoxy-3-oxo-1-propenyl)benzenesulfonylamino]carbonyl}amino)-4-chlorobenzoate. Properties: colorless amorphous, PMR (δ ppm, CDCl$_3$): 1.53 (9H, s), 3.95 (3H, s), 6.46 (1H, d), 7.05 (1H, d), 7.55 (1H, m), 7.57 (1H, d), 7.72 (1H, m), 7.93 (1H, m), 8.04 (1H, m), 8.27 (1H, s), 8.46 (1H, d), 11.05 (1H, br).

Then, from 2.18 g (4.4 mmol) of the resultant sulfonylurea product, in the same way, 698 mg (yield 37%: 3 steps) of the above-identified compound was obtained. Properties: colorless crystal, Melting point: >200° C. (decomposition), PMR (δ ppm, DMSO-$d_6$): 6.65 (1H, d), 7.12 (1H, s), 7.25 (1H, d), 7.69 (1H, d), 7.72 (1H, t), 7.87 (1H, d), 8.12 (2H, q), 8.37 (1H, s), 11.64 (1H, s).

Preparation Example 15

Synthesis of 4-[(7-chloro-2,4(1H,3H)-quinazolinedion-3-yl)sulfonyl]salicylic acid (Compound 15)

1.0 g (3.66 mmol) of 4-t-butoxycarbonyl-3-hydroxybenzenesulfonamide and 1.12 g (3.66 mmol) of methyl 4-chloro-2-N-phenoxycarbonylanthranilate were treated in the same way as in Preparation Example 7 to obtain 1.79 g (yield 100%) of methyl 2-{[(4-t-butoxycarbonyl-3-hydroxybenzenesulfonylamino)carbonyl]amino}-4-chlorobenzoate. Properties: colorless amorphous, PMR (δ ppm, DMSO-$d_6$): 1.57 (9H, s), 3.87 (3H, s), 7.14 (1H, d), 7.40–7.45 (2H, m), 7.85 (1H, d), 7.92 (1H, d), 8.32 (1H, d), 10.13 (1H, s), 10.82 (1H, s)

Then, from 1.78 g (3.66 mmol) of the resultant sulfonylurea product, in the same way, 370 mg (yield 25%: 3 steps) of the above-identified compound was obtained. Properties: colorless crystal, Melting point: >2000° C. (decomposition), PMR (δ ppm, DMSO-$d_6$): 7.13 (1H, s), 7.26 (1H, d), 7.69 (1H, d), 7.87 (1H, d), 8.01 (1H, d), 11.67 (1H, s).

Preparation Example 16

Synthesis of 4-[(7-chloro-2,4(1H,3H)-quinazolinedion-3-yl)sulfonyl]salicylic acid monosodium salt (Compound 16)

50 mg (0.13 mmol) of Compound 15 was suspended in approximately 1 ml of THF, then 126 μl of 1N sodium hydroxide aqueous solution was added dropwise. The solution was confirmed to have become uniform, then 30 ml of water was added and the mixture freeze-dried to quantitatively obtain the above-identified compound in an amorphous state in an amount of 52 mg. Properties: colorless amorphous, PMR (δ ppm, CD$_3$OD): 7.11 (1H, s), 7.19 (1H, d), 7.58 (1H, d), 7.63 (1H, s), 7.92 (1H, d), 8.03 (1H, d).

Preparation Example 17

Synthesis of 4-[(7-chloro-2,4(1H,3H)-quinazolinedion-3-yl)sulfonyl]anthranilic acid (Compound 17)

2.84. g (6.99 mmol) of 3-benzyloxycarbonylamino-4-t-butoxycarbonylbenzenesulfonamide and 2.67 g (6.99 mmol) of benzyl 4-chloro-2-N-phenoxycarbonylanthranilate were treated in the same way as in Preparation Example 8 to obtain 3.74 g (yield 77%) of benzyl 2-{[(3-benzyloxycarbonylamino-4-t-butoxycarbonylbenzenesulfonylamino)carbonyl]amino}-4-chlorobenzoate. Properties: colorless amorphous, PMR (δ ppm, DMSO-d$_6$): 1.54 (9H, s), 5.19 (2H, s), 5.34 (2H, s), 7.05 (1H, m), 7.34–7.58 (10H, m), 7.60 (1H, d), 7.90 (1H, d), 7.98 (1H, d), 8.50. (1H, br), 8.62 (1H, s), 10.00 (1H, br), 10.41 (1H, s).

Then, from 3.74 g (5.39 mmol) of the resultant sulfonylurea, in the same way, 690 mg (yield 30%: 2 steps) of t-butyl 4-[(7-chloro-2,4(1H,3H)-quinazolinedion-3-yl)sulfonyl]anthranilate was obtained, then this was subjected to a similar debutylation reaction to obtain 503 mg (yield 84%) of the above-identified compound. Properties: colorless crystal, Melting point: >200° C. (decomposition), PMR (δ ppm, DMSO-d$_6$): 7.14 (1H, s), 7.18 (1H, d), 7.25 (1H, d), 7.59 (1H, s), 7.87 (1H, d), 7.89 (1H, d), 11.62 (1H, s).

Preparation Example 18

Synthesis of 4-[(7-chloro-2,4(1H,3H)-quinazolinedion-3-yl)sulfonyl]anthranilic acid monosodium salt (Compound 18)

50 mg (0.13 mmol) of Compound 17 was suspended in approximately 1 ml of THF, then 126 μl of 1N sodium hydroxide aqueous solution was added dropwise. The solution was confirmed to have become uniform, then 30 ml of water was added and the mixture was freeze-dried to quantitatively obtain the above-identified compound in an amorphous state in an amount of 52 mg. Properties: colorless amorphous, PMR (δ ppm, DMSO-d$_6$): 7.11–7.22 (3H, m), 7.37 (1H, s), 7.83 (1H, d), 7.91 (1H, d).

Preparation Example 19

Synthesis of 3-(4-hydroxybenzenesulfonyl)-7-chloro-2,4(1H,3H)-quinazolinedione (Compound 19)

1.50 g (7.03 mmol) of 4-allyloxybenzenesulfonyl isocyanate and 1.2 g (7.03 mmol) of 4-chloroanthranilic acid were treated in the same way as in Preparation Example 5 to obtain 1.5 g (yield 53%) of 3-(4-allyloxybenzenesulfonyl)-7-chloro -2,4(1H,3H)-quinazolinedione. 500 mg (1.27 mmol) thereof was similarly treated to obtain 405 g of the above-identified compound (yield 90%). Properties: colorless crystal, Melting point: >200° C. decomposition), PMR (δ ppm, DMSO-d$_6$): 6.98 (2H, d), 7.11 (1H, s), 7.23 (1H, d), 7.85 (1H, d), 8.00 (2H, d), 11.25 (1H, br).

Preparation Example 20

Synthesis of 4-[(2,4(1H,3H)-quinazolinedion-3-yl)sulfonyl]salicylic acid (Compound 20)

618 mg (2.26 mmol) of 4-t-butoxycarbonyl-3-hydroxybenzenesulfonamide and 613 mg (2.26 mmol) of methyl 2-N-phenoxycarbonylanthranilate were treated in the same way as in Preparation Example 17 to obtain 792 mg (yield 78%) of methyl 2-{[(4-t-butoxycarbonyl-3-hydroxybenzene-sulfonylamino)carbonyl]amino}benzoate. Properties: colorless amorphous, PMR (δ ppm, CDCl$_3$): 1.60 (9H, s), 3.97 (3H, s), 7.09 (1H, t), 7.49–7.52 (2H, m), 7.65 (1H, d), 7.90 (1H, d), 8.01 (1H, dd), 8.33 (1H, d), 10.98 (1H, s), 11.18 (1H, s).

Then, from 790 mg (1.75 mmol) of the resultant sulfonylurea product, in the same way, 100 mg (yield 8%: 3 steps) of the above-identified compound was obtained. Properties: colorless crystal, Melting point: >200° C. (decomposition), PMR (δ ppm, DMSO-d$_6$): 7.13 (1H, d), 7.22 (1H, t), 7.63–7.69 (3H, m), 7.87 (1H, d), 8.01 (1H, d), 11.57 (1H, s).

Preparation Example 21

Synthesis of 5-[(7-chloro-2,4(1H,3H)-quinazolinedion-3-yl)sulfonyl]salicylic acid (Compound 21)

320 mg (1.17 mmol) of 3-t-butoxycarbonyl-4-hydroxybenzenesulfonamide and 447 mg (1.17 mmol) of benzyl 4-chloro-2-N-phenoxycarbonylanthranilate were treated in the same way as in Preparation Example 17 to obtain 611 mg (yield 93%) of benzyl 2-{[(3-t-butoxycarbonyl-4-hydroxybenzenesulfonylamino)carbonyl]amino}-4-chlorobenzoate. Properties: colorless amorphous, PMR (δ ppm, CDCl$_3$): 1.62 (9H, s), 5.35 (2H, s), 7.01–7.05 (2H, m), 7.37–7.41 (5H, m), 7.96(1H, d), 8.10 (1H, dd), 8.46–8.48 (2H, m), 10.99 (1H, s), 11.66 (1H, s).

Then, from 611 mg (1.09 mmol) of the resultant sulfonylurea product, in the same way, 114 mg (yield 33%: 3 steps) of the above-identified compound was obtained. Properties: colorless crystal, Melting point: >200° C. (decomposition), PMR (δ ppm, DMSO-d$_6$): 7.11 (1H, s), 7.19 (1H, d), 7.24 (1H, d), 7.86 (1H, d), 8.20 (1H, d), 8.56 (1H, s), 11.57 (1H, s).

Preparation Example 22

Synthesis of 3-(3-acetamide-4-methoxybenzenesulfonyl-7-chloro-2,4(1H,3H)-quinazolinedione (Compound 22)

500 mg (2.19 mmol) of 3-acetamide-4-methoxybenzenesulfonamide and 836 mg (2.19 mmol) of benzyl 4-chloro-2-N-phenoxycarbonylanthranilate were treated in the same way as in Preparation Example 8 to obtain 812 mg (yield 70%) of benzyl 2-{[(3-acetylamino-4-methoxybenzenesulfonylamino)carbonyl]amino}-4-chlorobenzoate. Properties: colorless amorphous, PMR (δ ppm, DMSO-d$_6$): 2.12 (3H, s), 3.93 (1H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 611 mg (1.09 mmol) of the resultant sulfonylurea product, in the same way, 250 mg (yield 39%: 2 steps) of the above-identified compound was obtained. Properties: colorless crystal, Melting point: >200° C. (decomposition), PMR (δ ppm, DMSO-d$_6$): 2.12 (3H, s), 3.95 (3H, s), 7.12 (1H, s), 7.23 (1H, d), 7.30 (1H, d), 7.85 (1H, d), 7.89 (1H, d), 8.80 (1H, s), 9.42 (1H, s), 11.59 (1H, br).

Preparation Example 23

Synthesis of 3-(3-amino-4-methoxybenzenesulfonyl)-7-chloro-2,4(1H,3H)-quinazolinedione (Compound 23)

400 mg (1.40 mmol) of 3-t-butoxycarbonylamino-4-methoxybenzenesulfonamide and 533 mg (1.40 mmol) of benzyl 4-chloro-2-N-phenoxycarbonylanthranilate were treated in the same way as in Preparation Example 17 to obtain 86 mg (yield 16%: 4 steps) of the above-identified compound. Properties: colorless crystal, Melting point: >200° C. (decomposition), PMR (δ ppm, DMSO-d6): 3.81 (3H, s), 7.26–7.37 (5H, m), 7.77 (1H, s), 7.90 (1H, d), 7.94 (1H, d), 11.73 (1H, s).

Preparation Example 24

Synthesis of 7-chloro-3-(4-methoxy-3-methylsulfonylaminobenzenesulfonyl)-2,4(1H,3H)-quinazolinedione (Compound 24)

500 mg (1.89 mmol) of 4-methoxy-3-methylsulfonylaminobenzenesulfonamide and 722 mg (1.89 mmol) of benzyl 4-chloro-2-N-phenoxycarbonylanthranilate were treated in the same way as in Preparation Example 8 to obtain 888 mg (yield 83%) of benzyl 2-({[(4-methoxy-3-methylsulfonylamino)benzene sulfonylamino]carbonyl}amino)-4-chlorobenzoate. Properties: colorless amorphous, PMR (δ ppm, DMSO-$d_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, S), 10.25 (1H, s), 12.11 (1H, br).

Then, from 880 mg (1.55 mmol) of the resultant sulfonylurea product, in the same way, 620 mg (yield 85%: 2 steps) of the above-identified compound was obtained. Properties: colorless crystal, Melting point: >200° C. (decomposition), PMR (δ ppm, DMSO-$d_6$): 3.04 (3H, s), 3.94 (3H, s), 7.11 (1H, s), 7.23 (1H, d), 7.34 (1H, d), 7.86 (1H, d), 7.99 (1H, d), 8.10 (1H, s).

Preparation Example 25

Synthesis of 4-[(7-chloro-2,4(1H,3H)-quinazolinedion-3-yl)sulfonyl]-1-hydroxy-naphthalene-2-carboxylic acid (Compound 25)

323 mg (1.00 mmol) of 3-t-butoxycarbonyl-4-hydroxy-1-naphthalenesulfonamide and 381 mg (1.00 mmol) of benzyl 4-chloro-2-N-phenoxycarbonylanthranilate were treated in the same way as in Preparation Example 17 to obtain 447 mg (yield 73%) of 4-({[(2-benzyloxycarbonyl-5-chloroanilino)carbonyl]amino}sulfonyl)-1-hydroxy-2-naphthalenecarboxylic acid t-butyl ester. Properties: colorless amorphous, PMR (δ ppm, DMSO-d6): 1.66 (9H, s), 5.34 (3H, s), 6.98 (1H, d), 7.35–7.48 (5H, m), 7.66 (1H, m), 7.81 (1H, m), 7.89 (1H, d), 8.37 (2H, m), 8.44 (1H, s), 8.71 (1H, d), 10.02 (1H, br), 12.52 (1H, br).

Then, from 445 mg (0.72 mmol) of the resultant sulfonylurea product, in the same way, 56 mg (yield 18%: 3 steps) of the above-identified compound was obtained. Properties: colorless crystal, Melting point: >200° C. (decomposition), PMR (δ ppm, DMSO-$d_6$): 7.08 (1H, s), 7.20 (1H, d), 7.63 (1H, t), 7.77 (1H, t), 7.84 (1H, d), 8.42 (1H, d), 8.51 (1H, d), 8.75 (1H, s), 11.57 (1H, s).

Preparation Example 26

Synthesis of 5-[(7-chloro-2,4(1H,3H)-quinazolinedion-3-yl)sulfonyl]anthranilic acid (Compound 26)

834 mg (2.05 mmol) of 4-benzyloxycarbonylamino-3-t-butoxycarbonylbenzenesulfonamide and 783 mg (2.05 mmol) of benzyl 4-chloro-2-N-phenoxycarbonylanthranilate were treated in the same way as in Preparation Example 17 to obtain 1.18 g (yield 83%) of benzyl 2-{[(4-benzyloxycarbonylamino-3-t-butoxycarbonylbenzenesulfonylamino)carbonyl]amino}-4-chlorobenzoate. Properties: colorless amorphous, PMR (δ ppm, CDCl$_3$): 1.56 (9H, s), 5.22 (2H, s), 5.37 (2H, s), 7.04 (1H, dd), 7.33–7.42 (10H, m), 7.97 (1H, d), 8.14 (1H, d), 8.45 (1H, d), 8.60 (1H, d), 8.65 (1H, d), 11.01 (1H, s), 11.11 (1H, s).

Then, from 1.17 g (1.69 mmol) of the resultant sulfonylurea product, in the same way, 404 mg (yield 60%: 3 steps) of the above-identified compound was obtained. Properties: colorless crystal, Melting point: >200° C. (decomposition), PMR (δ ppm, DMSO-$d_6$): 6.89 (1H, d), 7.11 (1H, s), 7.23 (1H, d), 7.85 (1H, d), 7.98 (1H, d), 8.51 (1H, s), 11.51 (1H, s).

Preparation Example 27

Synthesis of 4-[(7-methoxy-2,4(1H,3H)-quinazolinedion-3-yl)sulfonyl]anthranilic acid (Compound 27)

500 mg (1.23 mmol) of 3-benzyloxycarbonylamino-4-t-butoxycarbonylbenzenesulfonamide and 460 mg (1.22 mmol) of benzyl 4-methoxy-2-N-phenoxycarbonylanthranilate were treated in the same way as in Preparation Example 17 to obtain 15 mg (yield 3.1%: 4 steps) of the above-identified compound. Properties: colorless crystal, Melting point: >200° C. (decomposition), PMR (δ ppm, DMSO-$d_6$): 3.82 (3H, s), 6.58 (1H, s) 6.80 (1H, d), 7.16 (1H, d), 7.56 (1H, s), 7.80 (1H, d) 7.90 (1H, d), 11.49 (1H, s).

Preparation Example 28

Synthesis of (±)-7-[(7-chloro-2,4(1H,3H)-quinazolinedion-3-yl)sulfonyl]-2-oxo-1H,3H-quinoline-3-carboxylic acid (Compound 28)

400 mg (1.23 mmol) of (±)-3-t-butoxycarbonyl-2-oxo-1H,3H-quinoline-7-sulfonamide and 468 mg (1.23 mmol) of benzyl 4-chloro-2-N-phenoxycarbonylanthranilate were treated in the same way as in Preparation Example 17 to obtain 649 mg (yield 86%) of 8-({[(2-benzyloxycarbonyl-5-chloroanilino)carbonyl]amino}sulfonyl)-2-oxo-1,2,3,4-tetrahydro-3-quinoline carboxylic acid t-butyl ester. Properties: colorless amorphous, PMR (δ ppm, CDCl$_3$): 1.32 (9H, s), 3.18–3.30 (2H, m), 3.54 (1H, m), 5.35 (2H, s), 6.85 (1H, m), 7.00 (1H, m), 7.35–7.39 (5H, m), 7.87–7.96 (3H, m), 8.47 (1H, m), 8.78 (1H, br), 10.92 (1H, br).

Then, from 640 mg (1.04 mmol) of the resultant sulfonylurea product, in the same way, 258 mg (yield 55%: 3 steps) of the above-identified compound was obtained. Properties: colorless crystal, Melting point: >200° C. (decomposition), PMR (δ ppm, DMSO-$d_6$): 3.23–3.31 (2H, m), 3.59 (1H, t), 7.07 (1H, d), 7.12 (1H, s), 7.25 (1H, d), 7.86 (1H, d), 7.96 (1H, d), 7.98 (1H, d), 10.84 (1H, s), 11.60 (1H, s).

Preparation Example 29

Synthesis of (±)-6-[(7-chloro-2,4(1H,3H)-quinazolinedion-3-yl)sulfonyl]-3-oxo-1,4-benzoxazine-2-carboxylic acid (Compound 29)

300 mg (0.91 mmol) of (±)-2-t-butoxycarbonyl-3-oxo-1,4-benzoxazin-6-sulfonamide and 349 mg (0.91 mmol) of benzyl 4-chloro-2-N-phenoxycarbonylanthranilate were treated in the same way as in Preparation Example 17 to obtain 417 mg (yield 74%) of 5-({[(2-benzyloxycarbonyl- 5-chloroanilino)carbonyl]amino}sulfonyl)-3-oxo-3,4-dihydro-2H-1,4-benzoxazine-2-carboxylic acid t-butyl ester. Properties: colorless amorphous, PMR (δ ppm, DMSO-$d_6$): 1.29 (9H, s), 5.37 (2H, s), 5.42 (2H, s), 7.1,9–7.26 (2H, m), 7.37–7.57 (7H, m), 7.97 (1H, d), 8.25 (1H, d), 10.27 (1H, s), 11.25 (1H, s), 12.22 (1H, br).

Then, from 417 mg (0.68 mmol) of the resultant sulfonylurea product, in the same way, 100 mg (yield 32%: 3 steps) of the above-identified compound was obtained. Properties: colorless crystal, Melting point: >200° C. (decomposition), PMR (δ ppm, DMSO-$d_6$): 5.47 (1H, s), 7.11 (1H, s), 7.24 (1H, d), 7.29 (1H, d), 7.76 (1H, s), 7.78 (1H, d), 7.86 (1H, d), 11.25 (1H, s), 11.62 (1H, s).

Preparation Example 30

Synthesis of 4-[(7-hydroxy-2,4(1H,3H)-quinazolinedion-3-yl)sulfonyl]anthranilic acid (Compound 30)

620 mg (1.53 mmol) of 3-benzyloxycarbonylamino-4-t-butoxycarbonylbenzenesulfonamide and 550 mg (1.51 mmol) of benzyl 4-hydroxy-2-N-phenoxycarbonylanthranilate were treated in the same way as in Preparation Example 17 to obtain 25 mg (yield 4%: 4 steps) of the above-identified compound. Properties: colorless crystal, Melting point: >200° C. (decomposition), PMR (δ ppm, DMSO-$d_6$): 6.48 (1H, s), 6.61 (1H, d), 7.14 (1H, d), 7.51 (1H, s), 7.70 (1H, d), 7.90 (1H, d), 10.80 (1H, s), 11.39 (1H, s).

Preparation Example 31

Synthesis of 4-[(7-chloro-2,4(1H,3H)-quinazolinedion-3-yl)sulfonyl]-2-N-propionylanthranilic acid (Compound 31)

840 mg (1.86 mmol) of Compound 17 was dissolved in 8 ml of 1,4-dioxane, 240 μl (2.79 mmol) of propionyl chloride was added dropwise, then the resultant mixture was stirred overnight at 60° C. An excess of water was added to the reaction solution and the mixture was extracted with ethyl acetate. The organic layer thus obtained was washed, dried, and concentrated to obtain a crude product of t-butyl 4-[(7-chloro-2,4(1H,3H)-quinazolinedion-3-yl)sulfonyl]-2-N-propionylanthranilate. The obtained crude product was stirred at room temperature in 3 ml of trifluoroacetic acid for 1 hour, then the reaction solution was concentrated in vacuo to obtain a crude product. This was washed by diethyl ether to obtain 400 mg (yield 48%: 2 steps) of the above-identified compound. Properties: colorless crystal, Melting point: >200° C. (decomposition), PMR (δ ppm, DMSO-$d_6$): 1.10 (3H, t), 2.45 (2H, dd), 7.11 (1H, s), 7.24 (1H, d), 7.85 (1H, d), 7.88 (1H, d), 8.17 (1H, d), 9.18 (1H, s), 11.07 (1H, s), 11.63 (1H, s).

Preparation Example 32

Synthesis of 4-[(6-chloro-2,4(1H,3H)-quinazolinedion-3-yl)sulfonyl]anthranilic acid (Compound 32)

300 mg (0.74 mmol) of 3-benzyloxycarbonylamino-4-t-butoxycarbonylbenzenesulfonamide and 310 mg (0.81 mmol) of benzyl 5-chloro-2-N-phenoxycarbonylanthranilate were treated in the same way as in Preparation Example 17 to obtain 75 mg (yield 26%: 4 steps) of the above-identified compound. Properties: colorless crystal, Melting point: >200° C. (decomposition), PMR (δ ppm, DMSO-$d_6$): 7.13–7.20 (2H, m), 7.56 (1H, s), 7.72 (1H, d), 7.82 (1H, s), 7.90 (1H, d), 11.68 (1H, s).

Preparation Example 33

Synthesis of 4-[(7-chloro-2.4(1H,3H)-quinazolinedion-3-yl)sulfonyl]-2-N-methanesulfonylanthranilic acid (Compound 33)

200 mg (0.44 mmol) of Compound 17 was treated in the same way as in Preparation Example 3 to obtain 81 mg of t-butyl 4-[(7-chloro-2,4(1H,3H)-quinazolinedion-3-yl) sulfonyl]-2-N-methanesulfonylanthranilate. This was used to perform the same debutylation reaction to obtain 53 mg (yield 25%: 2 steps) of the above-identified compound. Properties: colorless crystal, Melting point: >200° C. (decomposition), PMR (δ ppm, DMSO-$d_6$): 3.24 (3H, s), 7.11 (1H, s), 7.25 (1H, d), 7.85–7.91 (2H, m), 8.23 (1H, d), 18.39 (1H, s), 11.05 (1H, br), 11.70 (1H, s).

Preparation Example 34

Synthesis of 3-(3-aminobenzenesulfonyl)-7-chloro-2,4-(1H,3H)quinazolinedion methanesulfonic acid salt (Compound 34)

2.15 g (6.10 mmol) of compound 12 was dissolved in 65 ml of THF and 0.4 ml of methanesulfonic acid was added dropwise. To this solution, 200 ml of ether was added and the resultant precipate was filtered to obtain 2.59 g (yield 95%) of the above-identified compound. Properties: colorless amorphous, PMR (δ ppm, DMSO-$d_6$): 2.35 (3H, s), 6.98 (1H, d), 7.12 (1H, m), 7.25 (1H, m), 7.34 (2H, s), 7.43 (1H, m), 7.86 (1H, s), 11.64 (1H, s).

Example 1

Measurement of Chymase Inhibitory Activity

Human heart chymase was purified according to the method of Urata et al. (*J. Biol. Chem.*, 1990, 265, 22348). The inhibitory activity off the compound of the present invention was determined as follows. Purified enzyme was diluted with 0.1M tris HCl buffer (pH=7.5), 1M sodium chloride, and 0.01% Triton X-100 to obtain an enzyme solution having appropriate concentrations. Suc-Ala-Ala-Pro-Phe-MCA (Peptide Institute Inc.) was dissolved in 10 mM dimethyl sulfoxide (hereinafter referred to as DMSO) and diluted 20-fold with 0.1 M Tris-HCl buffer (pH 7.5) containing 1 M sodium chloride and 0.01% Triton X-100 to an appropriate concentration to prepare substrate solution.

5 μl of the test sample in DMSO was added to 75 μl of the enzyme solution and preincubated at 30° C. for 10 minutes. Then, 20 μl of the subs rate solution was added to the test sample-enzyme mixture, and incubated at 30° C. Ten minutes later, 50 μl of 30% acetic acid was added to stop the enzymatic reaction, and the amount of AMC formed was determined using a fluorophotometer. At the same time, 5 μl of DMSO in stead of the test sample was added and reacted simultaneously as a control. The inhibitory activity to human chymase was calculated based on the value of the control, and then the inhibition percentage and the 50% inhibition concentration ($IC_{50}$) were determined.

The IC$_{50}$ values for representative compounds are shown in Table I.

TABLE I

| Example No. | IC$_{50}$ value ($\mu$M) |
|---|---|
| 1 | 0.36 |
| 2 | 0.14 |
| 8 | 0.035 |
| 10 | 0.17 |
| 12 | 0.44 |
| 13 | 0.3 |
| 16 | 0.84 |
| 17 | 0.14 |
| 18 | 0.14 |
| 21 | 0.34 |
| 22 | 0.3 |
| 24 | 0.32 |
| 27 | 4.0 |
| 29 | 1.7 |
| 32 | 1.5 |
| 34 | 0.36 |

Example 2
Effects of Chymase Inhibitor on Chymase Activity in Mice

A chymase inhibitor (Compound 18) was administered intraperitoneally in ICR mice (8 weeks old, n=3). After 12 hours and 24 hours, the chymase was extracted from the small intestines, tongues, back skins, front legs, and rear legs of the mice and the enzymatic activity thereof was determined. The chymase was extracted using a 10 mM phosphate buffer including 2M KCl and 0.1% polyethylene octylphenyl ether (Triton X-100) from the tissues. Chymase activity was determined, by measuring the rate of hydrolysis of synthesized substrate Suc-Phe-Pro-Phe-p-nitroanilide. Saline was administered in 24 hours in control groups.

Results

Administration of Compound 18 inhibited chymase activity in the intestines by approximately 80% compared with the group administered saline, whereas the inhibition by Compound 18 was about 50% in the tongue, back skin, and legs (see FIG. 1). These results show that the Compound 18 had an action in inhibiting chymase even in vivo.

Example 3
Determination of Chymase Activity in Tsk Mice, Model for Scleroderma

Collagen content, thickness of subcutaneous fibrous layer, mast cell number, chymase activity and chymase mRNA were measured in the skin of Tsk mice (Rheum. Dis. Clin. North Am. 16, 153, 1990), and compared with the control mice (pallid mice) at the ages of 5, 10, and 20 weeks (n=6). The collagen content was determined by measuring hydroxyproline, the marker for collagen, using HPLC, whereas fibrous layer thickness was determined by histological analysis with Azan staining followed by measuring the area of the fibrous layer using an image analysis system. The density of mast cells was calculated by counting the number of cells with stained granules by toluidine blue staining. Chymase was extracted from the skin according to the method described previously (Arch. Dermatol. Res. 290, 553, 1998), and the activity determined as described in Example 2. The mRNA for the skin chymase (MMCP-4) was measured only at 10 weeks of age by competitive RT-PCR method (Biotechniques 21, 268, 1996).

Results

Figure 2:
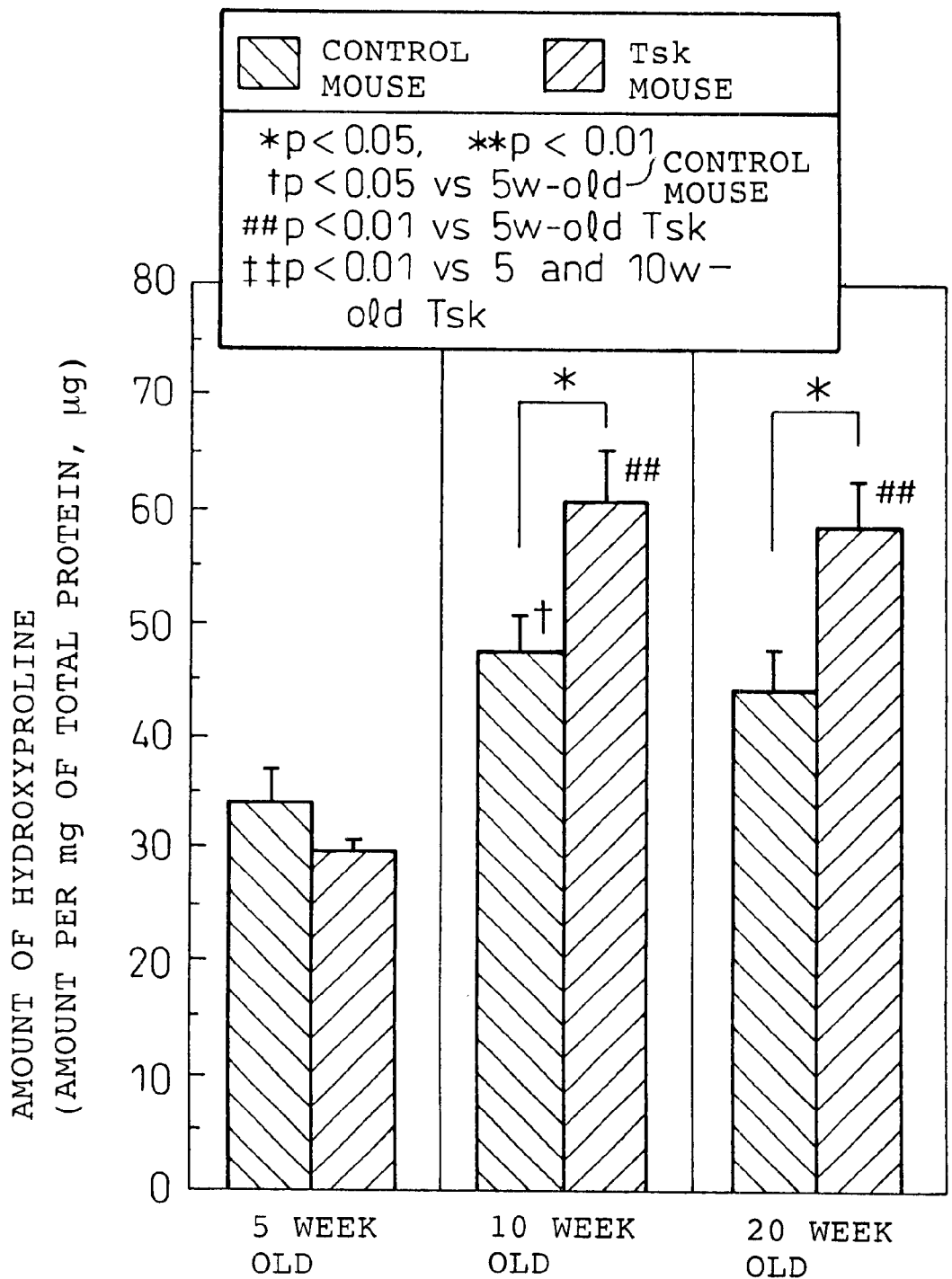
FIG. 2 is a graph showing the results of measurement of the content of skin collagen (hydroxyproline content) in Tsk mice in Example 3.
Figure 3:
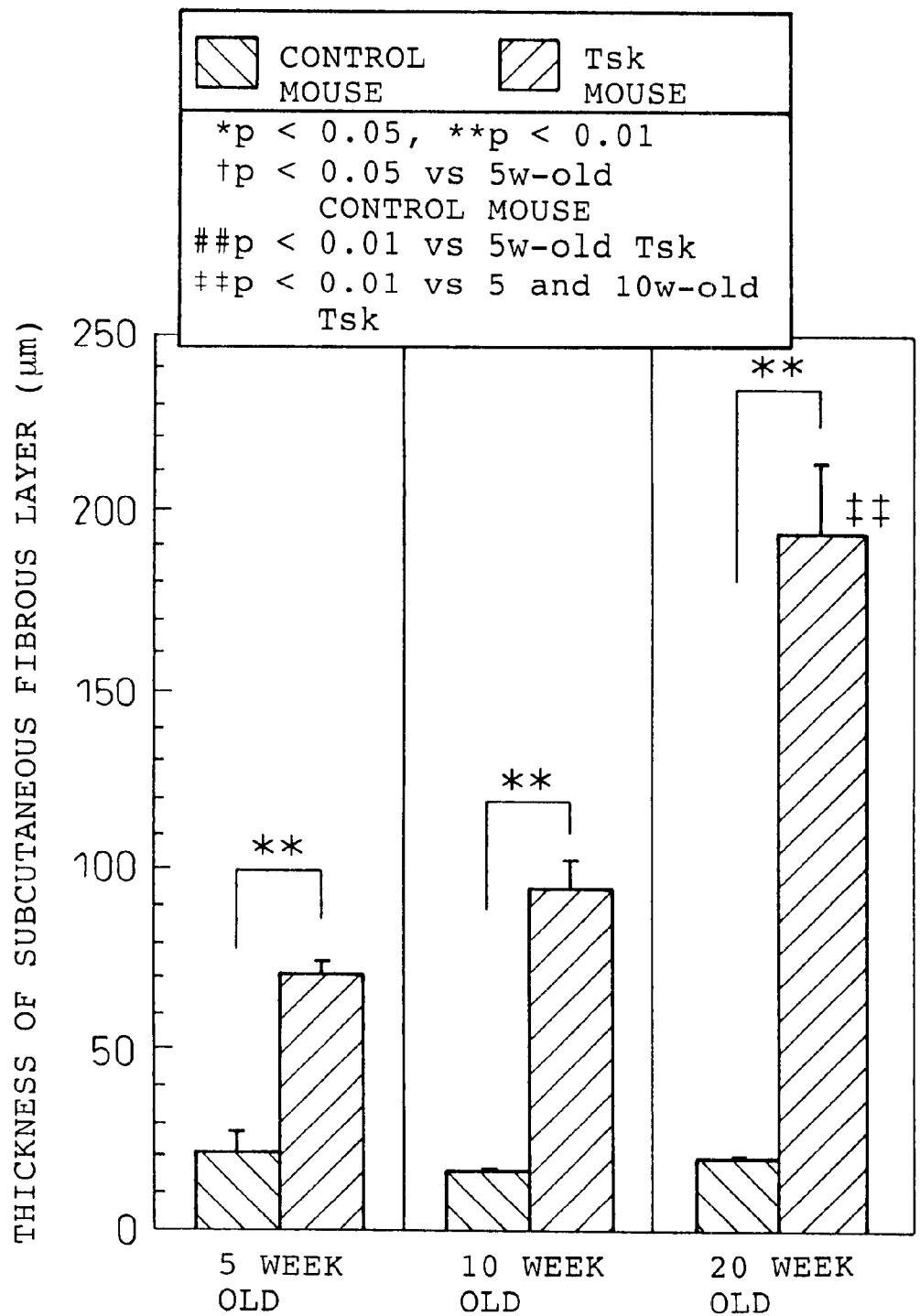
FIG. 3 is a graph showing the results of measurement of the degree of the thickness of subcutaneous fibrous layer in Tsk mice in Example 3.
Figure 4:
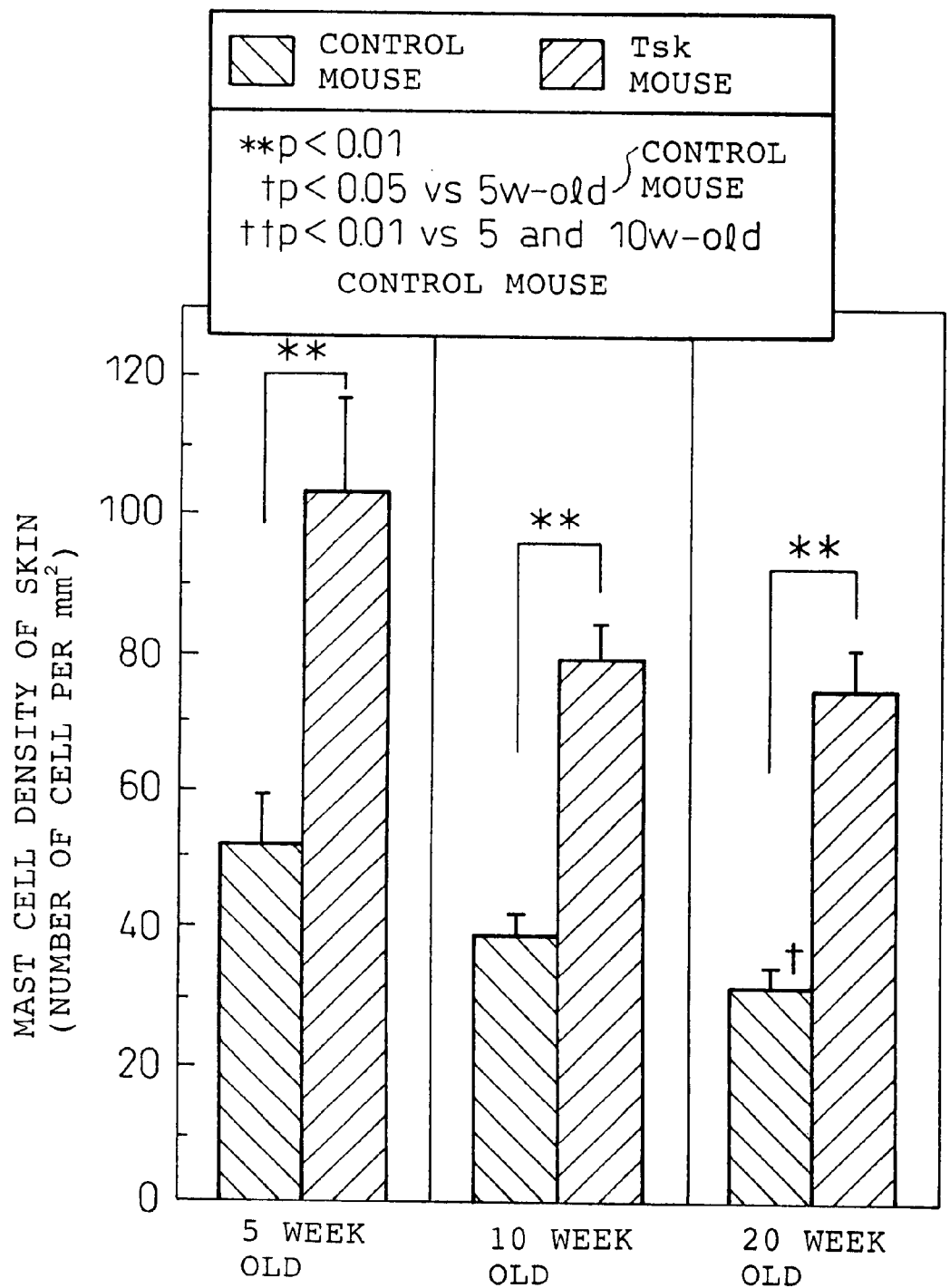
FIG. 4 is a graph showing the results of measurement of the mast cell density in the skin of Tsk mice in Example 3.
Figure 5:
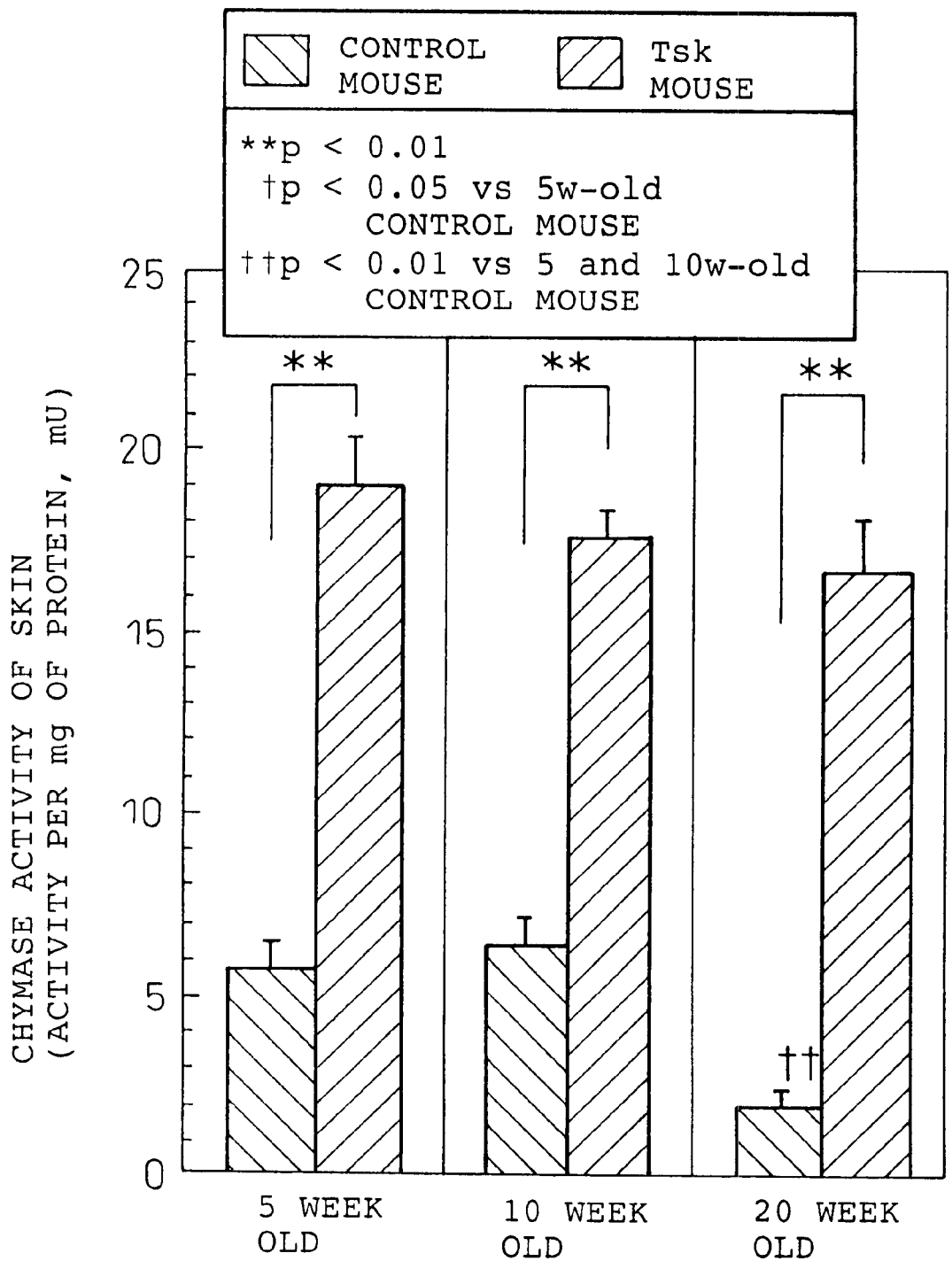
FIG. 5 is a graph showing the results of measurement of chymase activity in the skin of Tsk mice in Example 3.
Figure 6:
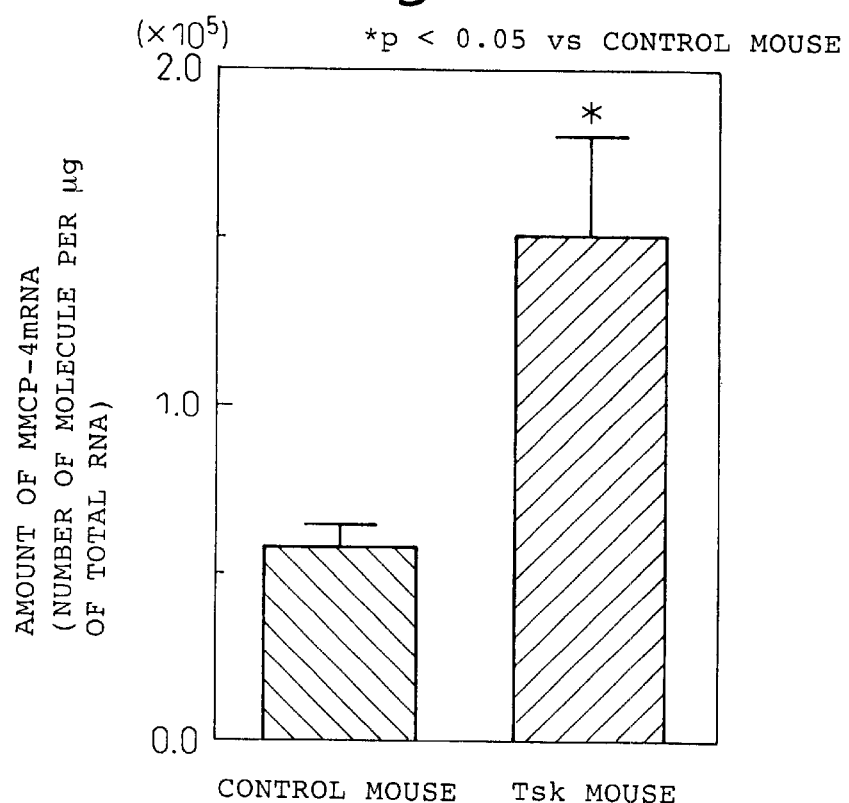
FIG. 6 is a graph showing the results of measurement of the mRNA content for the skin chymase of Tsk mice in Example 3.

The amount of skin hydroxyproline in Tsk mice was about the same as with the control pallid mice at 5 weeks of age, but was significantly higher than that of the controls at 10 and 20 weeks age (FIG. 2) (Student's t-test). Histological analysis revealed that there was remarkable hypertrophy of the fibrous layer in Tsk mice compared with the control mice at 5 weeks of age and that this difference became greater along with the increase in age (FIG. 3). The density of mist cells of the skin as well as the skin chymase activity in Tsk mice was higher than those of the control mice from 5 to 20 weeks age (FIG. 4 and FIG. 5). Further, the mRNA of the chymase MMCP-4 of 10 weeks aged mice was measured. The amount of mRNA of the MMCP-4 was significantly higher in value compared with that of the control mice (FIG. 6) as a result.

Example 4
Effect of Chymase Inhibitor Against Tsk Mice, Model for Scleroderma 13-week old Tsk mice (n=5) were intra peritoneally administered a chymase inhibitor (Compound 18) in a dosage of 50 mg/kg/day once a day every day for 2 weeks. Five hours after the final administration, the degree of hypertrophy of the subcutaneous fibrous layer and the skin-chymase activity were measured and compared with the values of the group administered saline. These parameters were measured in the same way as in Example 3.

Results

Figure 7:
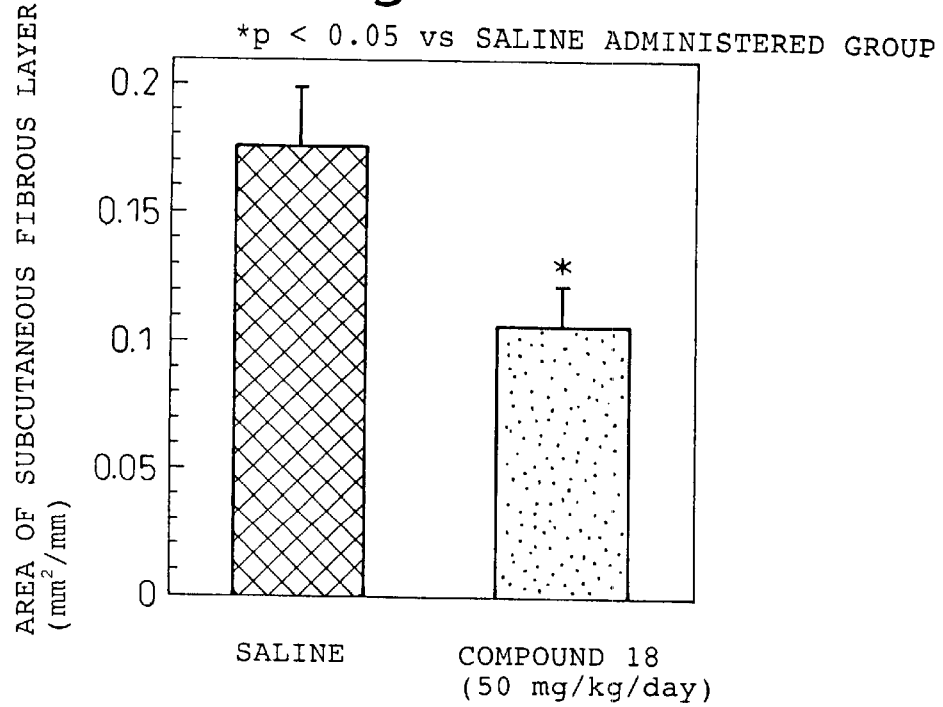
FIG. 7 is a graph showing the results of measurement of the thickness of subcutaneous fibrous layer in Tsk mice in Example 4.
Figure 8:
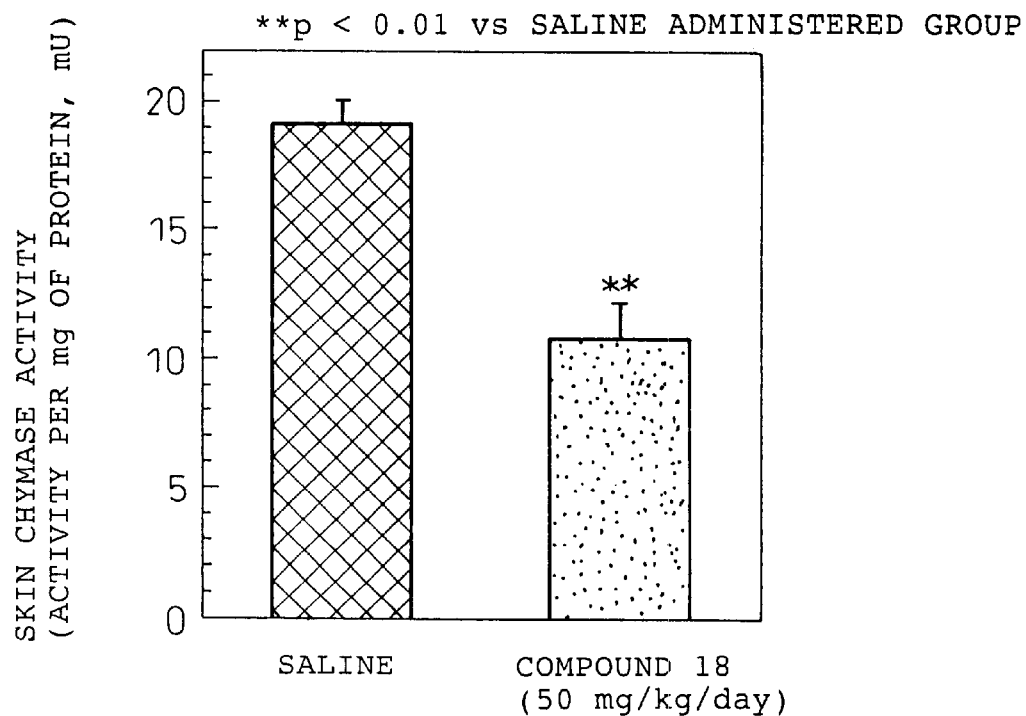
FIG. 8 is a graph showing the results of measurement of the chymase activity in the skin of Tsk mice in Example 4.

Pathohistological analysis revealed that the thickness of the subcutaneous fibrous layer in Tsk mice administered the Compound 18 was about 60% of that for the group administered saline (FIG. 7). On the other hand, the chymase activity in the group administered Compound 18 was 57% of that of the group administered saline (FIG. 8). These results show that a chymase inhibitor normalizes the abnormalities of the connective, tissue accumulation in various fibrotic diseases and is useful for the prevention or treatment of fibrogenesis.

Example 5
Change in Hydroxyproline Content in Lung in Bleomycin-Induced Pulmonary Fibrosis Model Pulmonary fibrosis was induced by intratracheal administration of bleomycin (Nippon Kayaku) to 10 week old male ICR mice (Charles River Japan) under anesthesia (n=10). That is, bleomycin (0.04 mg or 0.08 mg) was suspended in 50 $\mu$l of saline and administered into the airways using a 100 $\mu$l syringe (made by Hamilton Co.) Two weeks after the administration of bleomycin, the lungs were excised and the amount of hydroxyproline, an indicator of tissue collagen, was assayed according to the method as described previously (Anal. Biochem. 19, 249, 1967). Further, the amount of hydroxyproline was expressed as an amount per lung. Further, mice similarly administered saline instead of bleomycin were used as a control (n=10).

Results

Figure 9:
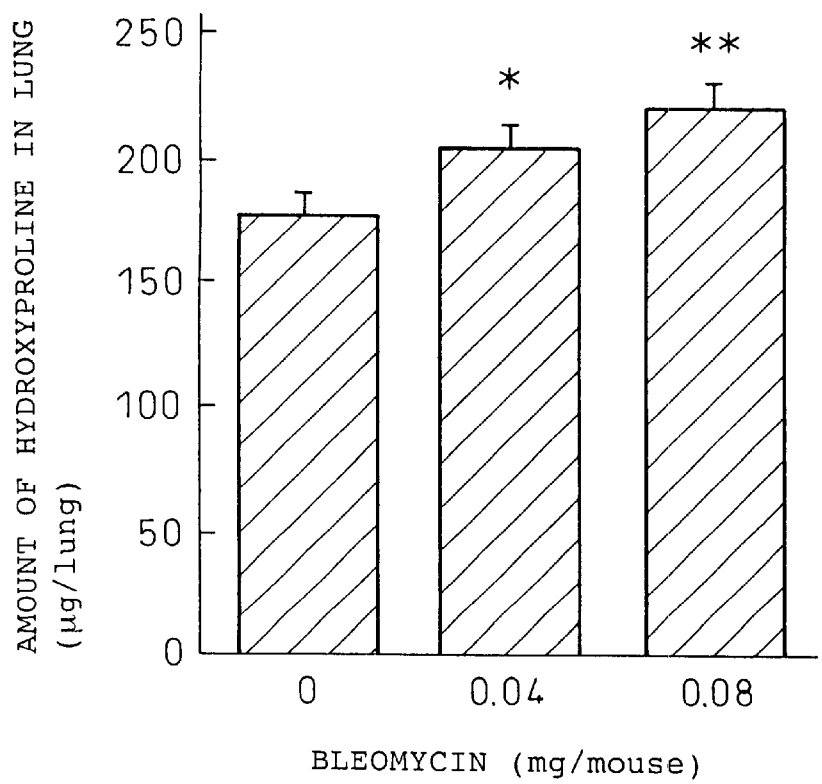
FIG. 9 is a graph showing the change of skin collagen content (hydroxyproline content) in the lung in bleomycin-induced pulmonary fibrosis model in mice. * and ** respectively indicate that P value of determination of significant difference (Dunnett's test) when compared with a control group (amount of administration of bleomycin of 0) is smaller than 0.05 and 0.01.

Administration of bleomycin increased hydroxyproline content in the lung in a dose-dependent manner (FIG. 9). The hydroxyproline contents were 1.15-fold and 1.25-fold at 0.04 mg/mouse and 0.08 mg/mouse, respectively, as compared with the saline group (p<0.05, p<0.01, respectively, Dunnett's test). This result shows that intratracheal administration of bleomycin induces lung fibrosis. In the following tests, the dosage of bleomycin was made of 0.08 mg.

Example 6
Change in Pulmonary Chymase Activity in Bleomycin-Induced Pulmonary Fibrosis Pulmonary fibrosis was induced by administration of 0.08 mg of bleomycin to mouse airways in accordance with the method described in Example 5 (n=3). The lungs were excised 2 weeks after administration, and the chymase activity was measured by the method described in Example 3. Note that mice similarly administered saline instead of bleomycin were used as the control (n=3).

Results

Figure 10:
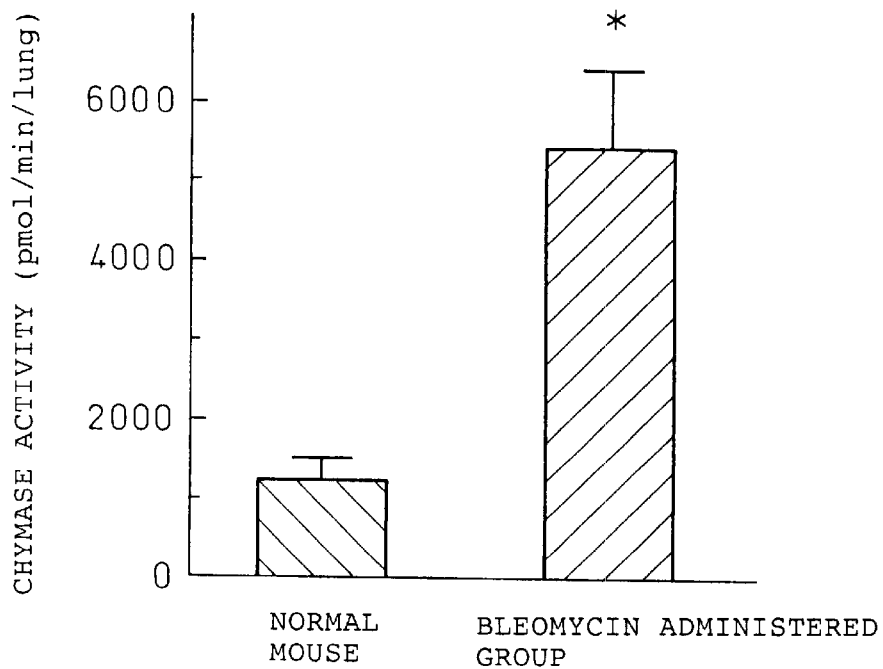
FIG. 10 is a graph showing the results of measurement of the chymase activity in the lung of bleomycin-induced mice. * indicates that P value of determination of significant difference (Student's t-test), when compared with normal mice, is smaller than 0.05.

The pulmonary chymase activity of mice administered bleomycin was significantly higher than that of mice administered saline (see FIG. 10) The activity of the group administered bleomycin was about 4.5 times that of the group administered saline (p<0.05, Student's t-test). The above findings that chymase activity increases in pulmonary fibrosis model suggests that chymase is involved in pathogenesis of pulmonary fibrosis.

Example 7

Effects of Chymase Inhibitor in Bleomycin-Induced Pulmonary Fibrosis Model

Pulmonary fibrosis was induced in accordance with the method described in Example 5 (n=10) and the amount of hydroxyproline in pulmonary tissue was assayed in the same way as in Example 5 in order to investigate the effect of a chymase inhibitor (Compound 34) on pulmonary fibrosis. Further, the chymase inhibitor was suspended in saline containing 0.5% hydroxypropyl cellulose (HPC/saline) and administered intraperitoneally at a dose of 10 mg/kg or 50 mg/kg once a day for five days a week over 2 weeks, starting immediately after the bleomycin administration. Further, a group similarly administered bleomycin but administered HPC/saline instead of compound 34 was used as the control.

Results

Figure 11:
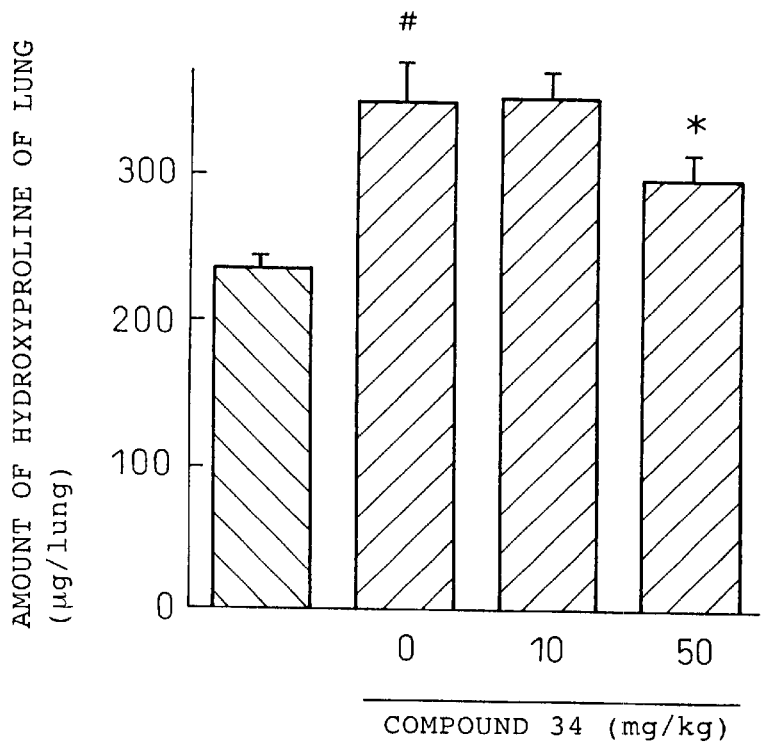
FIG. 11 is a graph showing the effect of chymase inhibitor on the content of skin collagen (hydroxyproline content) in the lung of a bleomycin-induced mice pulmonary fibrosis model. # indicates that P value of determination of significant difference (Student's t-test), when compared with a group administered saline, is smaller than 0.01, while * indicates that P-value of determination of significant difference (Dunnett's test), when compared with a group administered HPC/saline, is smaller than 0.05.

The chymase inhibitor (Compound 34) at a dose of 50 mg/kg significantly suppressed the increase of the amount of hydroxyproline in the lung caused by the administration of bleomycin (p<0.05, Dunnett's test). This rate of suppression was about 46% (FIG. 11). Compound 34 at 10 mg/kg exhibited little effect in this model.

In summary, the studies have been conducted using animal models for scleroderma (fibrosis of the skin) and pulmonary fibrosis in order to elucidate the usefulness of a chymase inhibitor in various types of fibrosis. The results show that the number of mast cells as well as chymase activity and its mRNA are increased in Tsk mice as compared with the control mice along with the increase of skin fibrous layer (Example 3). The administration of the chymase inhibitor Compound 18 suppressed the chymase activity and significantly suppressed the increase of the skin fibrous layer (Example 4). Further, in a bleomycin pulmonary fibrosis model, there was not only an increase in the amount of hydroxyproline in the lung, the marker for pulmonary fibrosis (Example 5), but also an increase in chymase activity in the lung (Example 6). The administration of the chymase inhibitor Compound 34 suppressed the increase in the amount of hydroxyproline (Example 7). These results suggest that a chymase inhibitor alleviates extracellular matrix dysbolism and is useful for the prevention or treatment of various types of fibrosis including scleroderma and pulmonary fibrosis.

Formulation Example 1

Production of Tablets 100.0 g of Compound 1 was mixed with microcrystalline cellulose in an amount of 22.5 g and magnesium stearate in an amount of 2.5 g and then tabletized by a single-action type tabletizing machine to produce tablets each containing 200 mg of Compound 1 and having a diameter of 9 mm and a weight of 250 mg.

Formulation Example 2

Production of Granules 30 g of Compound 1 was mixed well with lactose in an amount of 265 g and magnesium stearate in an amount of 5 g. The mixture was pressed molded, then pulverized and the granules sieved to obtain excellent 10% granules of 20 to 50 mesh.

Formulation Example 3

Production of Suppository

Vitepsol H-15 (made by Dynamite Nobel Co.) was warmed to melt. To this was added Compound 1 to a concentration of 12.5 mg/ml. This was homogeneously mixed, then was added in 2 ml amounts to a rectal suppository mold and cooled to obtain rectal suppositories each containing 25 mg of the Compound 1.

INDUSTRIAL APPLICABILITY

According to the present invention, a chymase inhibitor can effectively prevent and/or treat fibrosis in the skin and other organs through its effect of alleviating extracellular matrix dysbolism.

What is claimed is:

1. A method for the prevention or treatment of fibrosis involving extracellular matrix dysbolism comprising administering to a patient in need of such treatment a chymase inhibitor in an amount effective for prevention or treatment of said fibrosis.

2. A method for prevention or treatment according to claim 1, wherein the fibrosis involving extracellular matrix dysbolism is at least one disease selected from the group consisting of scleroderma, pulmonary fibrosis, benign prostatomegaly, myocardial fibrogenesis following myocardial infarction, myocardial fibrosis, musculoskeletal fibrosis, post-surgical adhesion, hypertropic scars and keloids, cirrhosis, hepatic fibrosis, renal fibrosis and fibrous vascular disorders.

3. A method for prevention or treatment according to claim 2, wherein siad fibrosis involving extracellular matrix dysbolism is a complication of diabetes selected from the group consisting of retinitis due to fibrous microvasculitis, neurosis, nephropathy, and peripheral arteritis.

4. A method for treatment as claimed in claim 1, wherein the chymase inhibitor is a quinazoline derivative having the following formula (I) or a pharmaceutically acceptable salt thereof:

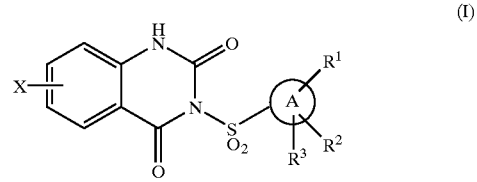

wherein the ring A represents an aryl group;

$R^1$ represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, a $C_1$ to $C_4$ lower alkyl group substituted with a carboxylic acid group, or a $C_2$ to $C_4$ lower alkylene group which may optionally be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, or a carboxylic acid group or when the ring A is a benzene ring, $R^1$ and $R^2$ may form, together with the substituting benzene ring, a fused heterocyclic ring which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

5. A method for the prevention or treatment of fibrosis involving extracellular matrix dysbolism comprising administering to a patient in need of such treatment a chymase inhibitor in an amount effective for prevention or treatment of said fibrosis, wherein the chymase inhibitor is a quinazoline derivative having the following formula (I) or a pharmaceutically acceptable salt thereof:

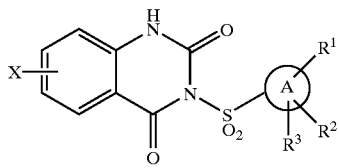

(I)

wherein
the ring A represents an aryl group;
R1 represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, a $C_1$ to $C_4$ lower alkyl group substituted with a carboxylic acid group, or a $C_2$ to $C_4$ lower alkylene group which may optionally be substituted with a carboxylic acid group;

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, or a carboxylic acid group or when the ring A is a benzene ring, $R^1$ and $R^2$ may form, together with the substituting benzene ring, a fused heterocyclic ring which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

6. A method for the prevention or treatment of fibrosis involving extracellular matrix dysbolism comprising administering to a patient in need of such treatment a chymase inhibitor in an amount effective for prevention or treatment of said fibrosis, wherein said chymase inhibitor is selected from the group consisting of α-keto acid derivatives, α,α-difluoro-β-keto acid derivatives, tripeptide inhibitors, phosphoric acid derivatives, trifluoromethylketone derivatives, acetoamide derivatives, triazine derivatives, phenol ester derivatives, cephem derivatives, isoxazole derivatives, imidazolidine derivatives, hydantoin derivatives and quinazoline derivatives.

7. A method for treating extracellular matrix dysbolism comprising administering to a patient in need of such treatment a chymase inhibitor in an amount effective for treating extracellular matrix dysbolism.

8. A method for treatment as claimed in claim 7, wherein the chymase inhibitor is a quinazoline derivative having the following formula (I) or a pharmaceutically acceptable salt thereof:

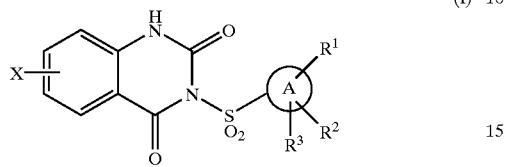

wherein
the ring A represents an aryl group;
$R^1$ represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, a $C_1$ to $C_4$ lower alkyl group substituted with a carboxylic acid group, or a $C_2$ to $C_4$ lower alkylene group which may optionally be substituted with a carboxylic acid group;
$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, or a carboxylic acid group or when the ring A is a benzene ring, $R^1$ and $R^2$ may form, together with the substituting benzene ring, a fused heterocyclic ring which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

9. A method for treating extracellular matrix dysbolism comprising administering to a patient in need of such treatment a chymase inhibitor in an amount effective for treating extracellular matrix dysbolism,
wherein the chymase inhibitor is a quinazoline derivative having the following formula (I) or a pharmaceutically acceptable salt thereof:

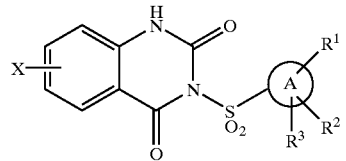

wherein
the ring A represents an aryl group;
$R^1$ represents a hydroxyl group, an amino group, a $C_1$ to $C_4$ lower alkylamino group which may optionally be substituted with a carboxylic acid group, a $C_7$ to $C_{10}$ lower aralkylamino group which may optionally be substituted with a carboxylic acid group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, a $C_1$ to $C_4$ lower alkyl group substituted with a carboxylic acid group, or a $C_2$ to $C_4$ lower alkylene group which may optionally be substituted with a carboxylic acid group;
$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may optionally be substituted with a carboxylic acid group, an amino group acylated with an aromatic ring carboxylic acid which may optionally be substituted with a carboxylic acid group, an amino group acylated with a heteroaromatic ring carboxylic acid which may optionally be substituted with a carboxylic acid group, an amino group sulfonylated with a $C_1$ to $C_4$ lower alkanesulfonic acid which may optionally be substituted with a carboxylic acid group, an amino group sulfonylated with an aromatic ring sulfonic acid which may optionally be substituted with a carboxylic acid group, an amino group sulfonylated with a heteroaromatic ring sulfonic acid which may optionally be substituted with a carboxylic acid group, or a carboxylic acid group or when the ring A is a benzene ring, $R^1$ and $R^2$ may form, together with the substituting benzene ring, a fused heterocyclic ring which may optionally be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

10. A method for the prevention or treatment of fibrosis involving extracellular matrix dysbolism comprising administering to a patient in need of such treatment a chymase inhibitor in an amount effective for prevention or treatment of said fibrosis, wherein said chymase inhibitor is selected from the group consisting of α-keto acid derivatives, α,α-difluoro-β-keto acid derivatives, tripeptide inhibitors, phosphoric acid derivatives, trifluoromethylketone derivatives, acetoamide derivatives, triazine derivatives, phenol ester derivatives, cephem derivatives, isoxazole derivatives, imidazolidine derivatives, hydantoin derivatives and quinazoline derivatives.

11. A method for treating extracellular matrix dysbolism comprising administering to a patient in need of such treatment a chymase inhibitor in an amount effective for treating extracellular matrix dysbolism, wherein said chymase inhibitor is selected from the group consisting of α-keto acid derivatives, α,α-difluoro-β-keto acid derivatives, tripeptide inhibitors, phosphoric acid derivatives, trifluoromethylketone derivatives, acetoamide derivatives, triazine derivatives, phenol ester derivatives, cephem derivatives, isoxazole derivatives, imidazolidine derivatives, hydantoin derivatives and quinazoline derivatives.

12. A method according to claim 5, wherein the aryl group represented by the ring A is selected from the group consisting of a benzene ring and a naphthalene ring.

13. A method according to claim 5, wherein the $C_1$ to $C_4$ lower alkylamino group which may optionally be substituted with the carboxylic acid group is selected from the group consisting of a methylamino group, an ethylamino group, a propylamino group, a butylamino group, a carboxymethylamino group, a carboxyethylamino group, a carboxypropylamino group, and a carboxybutylamino group.

14. A method according to claim 5, wherein the $C_7$ to $C_{12}$ lower aralkylamino group which may be substituted with the carboxylic acid group represented by $R^1$ is selected from the group consisting of a benzylamino group, a phenetylamino group, a phenylpropylamino group, a phenylbutylamino group, a carboxybenzylamino group, a carboxyphenetylamino group, a carboxyphenylpropylamino group, and a carboxyphenylbutylamino group.

15. A method according to claim 5, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

16. A method according to claim 5, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are each independently selected from the group consisting of a methanesulfonylamino group, an ethanesulfonylamino group, a propanesulfonylamino group, a butanesulfonyl amino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutane-sulfonylamino group, a carboxybenzenesulfonylamino group, a carboxynaphthalenesulfonylamino group, a carboxypyridinesulfonylamino group, and a carboxypyrrolesulfonylamino group.

17. A method according to claim 5, wherein the $C_1$ to $C_4$ lower alkyl group substituted with a carboxylic acid group represented by $R^1$ is selected from the group consisting of an acetic acid group, a propionic acid group, a butyric acid group, and a valeric acid group.

18. A method according to claim 5, wherein the $C_2$ to $C_4$ lower alkylene group substituted with a carboxylic acid group represented by $R^1$ is selected from the group consisting of an acrylic acid group and a crotonic acid group.

19. A method according to claim 5, wherein the unsubstituted or substituted $C_1$ to $C_4$ lower alkyl group represented by $R^2$ or $R^3$ is selected from the group consisting of a straight-chain alkyl group and a branched alkyl group.

20. A method according to claim 19, wherein the branched alkyl group is selected from the group consisting of an isopropyl group, a sec-butyl group, and a t-butyl group.

21. A method according to claim 5, wherein the substituent group of the $C_1$ to $C_4$ lower alkyl group is selected from the group consisting of a carboxylic acid group, a halogen atom, a $C_1$ to $C_4$ lower alkoxy group, an amino group, a methylamino group, a dimethylamino group, a carboxymethylamino group, and a carboxyethylamino group.

22. A method according to claim 5, wherein the halogen atom represented by $R^2$ or $R^3$ is selected from the group consisting of a fluorine atom, a chlorine atom, a bromine atom and an iodine atom.

23. A method according to claim 5, wherein the $C_1$ to $C_4$ lower alkoxyl group represented by $R^2$ or $R^3$ is selected from the group consisting of a straight-chain alkyloxy group and a branched alkyloxy group.

24. A method according to claim 23, wherein the straight-chain alkyloxy group is selected from the group consisting of a methoxy group, an ethoxy group, a n-propyloxy group, and a n-butoxy group.

25. A method according to claim 23, wherein the branched alkyloxy group is selected from the group consisting of an isopropyloxy group, a sec-butoxy group, and a t-butoxy group.

26. A method according to claim 5, wherein the unsubstituted or substituted $C_1$ to $C_4$ lower alkylamino group represented by $R^2$ or $R^3$ is selected from the group consisting of a methylamino group, an ethylamino group, a propylamino group, and a butylamino group.

27. A method according to claim 5, wherein the substituent group of the $C_1$ to $C_4$ lower alkylamino group is selected from the group consisting of a carboxylic acid group, a halogen atom, and a $C_1$ to $C_4$ lower alkoxyl group.

28. A method according to claim 5, wherein the unsubstituted or substituted $C_7$ to $C_{12}$ lower aralkylamino group represented by $R^2$ or $R^3$ is selected from the group consisting of a benzylamino group, a phenetylamino group, a phenylpropylamino group, and a phenylbutylamino group.

29. A method according to claim 5, wherein the substituent group of the aralkylamino group is selected from the group consisting of a carboxylic acid group, a halogen atom, and a $C_1$ to $C_4$ lower alkoxyl group.

30. A method according to claim 5, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

31. A method according to claim 5, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are each independently selected from the group consisting of a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridine-sulfonylamino group, and a carboxypyrrolesulfonylamino group.

32. A method according to claim 5, wherein the fused heterocyclic ring which may be substituted with a carboxylic acid and in which the carbon atom in the ring may form a carbonyl group which $R^1$ and $R^2$ form together with the substituting benzene ring when the ring A is a benzene ring, is selected from the group consisting of a tetrahydroquinoline, a benzoxazine, a quinoxaline, a benzodioxane, a carboxytetrahydroquinoline, a carboxybenzoxazine, a carboxyquinoxaline, and a carboxybenzodioxane.

33. A method according to claim 5, wherein the $C_1$ to $C_4$ lower alkyl group represented by X is selected from the group consisting of a methyl group, an ethyl group, a n-propyl group, a n-butyl group, an isopropyl group, a sec-butyl group, and a t-butyl group.

34. A method according to claim 5, wherein the $C_1$ to $C_4$ lower alkoxyl group represented by X is selected from the group consisting of a methoxy group, an ethoxy group, a n-propyloxy group, a n-butoxy group, an isopropyloxy group, a sec-butoxy group, and a t-butoxy group.

35. A method according to claim 5, wherein the halogen atom represented by X, is selected from the group consisting of a fluorine atom, a chlorine atom, a bromine atom and an iodine atom.

36. A method according to claim 5, wherein the pharmaceutically acceptable salt is selected from the group consisting of an acid salt and an alkali metal salt.

37. A method according to claim 5, wherein the pharmaceutically acceptable salt is selected from the group consisting of a hydrochloric acid salt, a methanesulfonic acid salt, a trifluoroacetic acid salt, a sodium salt and a potassium salt.

38. A method according to claim 9, wherein the aryl group represented by the ring A is selected from the group consisting of a benzene ring and a naphthalene ring.

39. A method according to claim 9, wherein the $C_1$ to $C_4$ lower alkylamino group which may optionally be substituted with the carboxylic acid group is selected from the group consisting of a methylamino group, an ethylamino group, a propylamino group, a butylamino group, a carboxymethylamino group, a carboxyethylamino group, a carboxypropylamino group, and a carboxybutylamino group.

40. A method according to claim 9, wherein the $C_7$ to $C_{12}$ lower aralkylamino group which may be substituted with the carboxylic acid group represented by $R^1$ is selected from the group consisting of a benzylamino group, a phenetylamino group, a phenylpropylamino group, a phenylbutylamino group, a carboxybenzylamino group, a carboxyphenetylamino group, a carboxyphenylpropylamino group, and a carboxyphenylbutylamino group.

41. A method according to claim 9, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

42. A method according to claim 9, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are each independently selected from the group consisting of a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutane-sulfonylamino group, a carboxybenzenesulfonylamino group, a carboxynaphthalenesulfonylamino group, a carboxypyridinesulfonylamino group, and a carboxypyrrolesulfonylamino group.

43. A method according to claim 9, wherein the $C_1$ to $C_4$ lower alkyl group substituted with a carboxylic acid group represented by $R^1$ is selected from the group consisting of an acetic acid group, a propionic acid group, a butyric acid group, and a valeric acid group.

44. A method according to claim 9, wherein the $C_2$ to $C_4$ lower alkylene group substituted with a carboxylic acid group represented by $R^1$ is selected from the group consisting of an acrylic acid group and a crotonic acid group.

45. A method according to claim 9, wherein the unsubstituted or substituted $C_1$ to $C_4$ lower alkyl group represented by $R^2$ or $R^3$ is selected from the group consisting of a straight-chain alkyl group and a branched alkyl group.

46. A method according to claim 45, wherein the branched alkyl group is selected from the group consisting of an isopropyl group, a sec butyl group, and a t-butyl group.

47. A method according to claim 9, wherein the substituent group of the $C_1$ to $C_4$ lower alkyl group is selected from the group consisting of a carboxylic acid group, a halogen atom, a $C_1$ to $C_4$ lower alkoxy group, an amino group, a methylamino group, a dimethylamino group, a carboxymethylamino group, and a carboxyethylamino group.

48. A method according to claim 9, wherein the halogen atom represented by $R^2$ or $R^3$ is selected from the group consisting of a fluorine atom, a chlorine atom, a bromine atom and an iodine atom.

49. A method according to claim 9, wherein the $C_1$ to $C_4$ lower alkoxyl group represented by $R^2$ or $R^3$ is selected from the group consisting of a straight-chain alkyloxy group and a branched alkyloxy group.

50. A method according to claim 49, wherein the straight-chain alkyloxy group is selected from the group consisting of a methoxy group, an ethoxy group, a n-propyloxy group, and a n-butoxy group.

51. A method according to claim 49, wherein the branched alkyloxy group is selected from the group consisting of an isopropyloxy group, a sec-butoxy group, and a t-butoxy group.

52. A method according to claim 9, wherein the unsubstituted or substituted $C_1$ to $C_4$ lower alkylamino group represented by $R^2$ or $R^3$ is selected from the group consisting of a methylamino group, an ethylamino group, a propylamino group, and a butylamino group.

53. A method according to claim 9, wherein the substituent group of the $C_1$ to $C_4$ lower alkylamino group is selected from the group consisting of a carboxylic acid group, a halogen atom, and a $C_1$ to $C_4$ lower alkoxyl group.

54. A method according to claim 9, wherein the unsubstituted or substituted $C_7$ to $C_{12}$ lower aralkylamino group represented by $R^2$ or $R^3$ is selected from the group consisting of a benzylamino group, a phenetylamino group, a phenylpropylamino group, and a phenylbutylamino group.

55. A method according to claim 9, wherein the substituent group of the aralkylamino group is selected from the group consisting of a carboxylic acid group, a halogen atom, and a $C_1$ to $C_4$ lower alkoxyl group.

56. A method according to claim 9, wherein the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are each independently selected from the group consisting of a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, and a carboxypyrrolecarbonylamino group.

57. A method according to claim 9, wherein the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are each independently selected from the group consisting of a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridine-sulfonylamino group, and a carboxypyrrolesulfonylamino group.

58. A method according to claim 9, wherein the fused heterocyclic ring which may be substituted with a carboxylic acid and in which the carbon atom in the ring may form a carbonyl group which $R^1$ and $R^2$ form together with the substituting benzene ring when the ring A is a benzene ring, is selected from the group consisting of a tetrahydroquinoline, a benzoxazine, a quinoxaline, a benzodioxane, a carboxytetrahydroquinoline, a carboxybenzoxazine, a carboxyquinoxaline, and a carboxybenzodioxan.

59. A method according to claim 9, wherein the $C_1$ to $C_4$ lower alkyl group represented by X is selected from the group consisting of a methyl group, an ethyl group, a n-propyl group, a n-butyl group, an isopropyl group, a sec-butyl group, and a t-butyl group.

60. A method according to claim 9, wherein the $C_1$ to $C_4$ lower alkoxyl group represented by X is selected from the group consisting of a methoxy group, an ethoxy group, a n-propyloxy group, a n-butoxy group, an isopropyloxy group, a sec-butoxy group, and a t-butoxy group.

61. A method according to claim 9, wherein the halogen atom represented by X, is selected from the group consisting of a fluorine atom, a chlorine atom, a bromine atom and an iodine atom.

62. A method according to claim 9, wherein the pharmaceutically acceptable salt is selected from the group consisting of an acid salt and an alkali metal salt.

63. A method according to claim 62, wherein the pharmaceutically acceptable salt is selected from the group consisting of a hydrochloric acid salt, a methanesulfonic acid salt, a trifluoroacetic acid salt, a sodium salt and a potassium salt.

* * * * *